US012667691B2

(12) United States Patent
Nishigishi

(10) Patent No.: US 12,667,691 B2
(45) Date of Patent: Jun. 30, 2026

(54) CATHETER

(71) Applicant: ASAHI INTECC CO., LTD., Seto (JP)

(72) Inventor: Makoto Nishigishi, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 474 days.

(21) Appl. No.: 18/225,745

(22) Filed: Jul. 25, 2023

(65) Prior Publication Data

US 2023/0381452 A1 Nov. 30, 2023

Related U.S. Application Data

(63) Continuation of application No. PCT/JP2021/041145, filed on Nov. 9, 2021.

(30) Foreign Application Priority Data

Feb. 2, 2021 (JP) ................................. 2021-014792

(51) Int. Cl.
A61M 25/00 (2006.01)

(52) U.S. Cl.
CPC ...... A61M 25/005 (2013.01); A61M 25/0032 (2013.01)

(58) Field of Classification Search
CPC .............. A61M 25/005; A61M 25/003; A61M 25/0032; A61M 25/007; A61M 25/0071; A61M 2025/0183; A61M 2025/018; A61M 2025/0197
See application file for complete search history.

(56) References Cited

U.S. PATENT DOCUMENTS

| | | | | |
|---|---|---|---|---|
| 5,374,245 A | * | 12/1994 | Mahurkar | ........... A61M 25/005 604/43 |
| 2004/0193034 A1 | | 9/2004 | Wasicek et al. | |
| 2005/0101870 A1 | | 5/2005 | Yamaguchi et al. | |
| 2006/0129091 A1 | * | 6/2006 | Bonnette | ................ A61B 17/22 604/93.01 |
| 2007/0185416 A1 | * | 8/2007 | Melsheimer | .......... A61M 25/09 600/585 |
| 2012/0095448 A1 | * | 4/2012 | Kajii | ..................... A61M 29/00 604/528 |

(Continued)

FOREIGN PATENT DOCUMENTS

| | | |
|---|---|---|
| CN | 107148289 A | 9/2017 |
| CN | 111918690 A | 11/2020 |
| JP | 4065167 B2 | 3/2008 |

(Continued)

*Primary Examiner* — Katrina M Stransky
(74) *Attorney, Agent, or Firm* — Oliff PLC

(57) ABSTRACT

A catheter having a shaft including a wire lumen, a sensor lumen that is arranged side by side with the wire lumen, a projection part that includes the wire lumen, projects to the more distal side than the distal end of the sensor lumen, and has a distal end opening in communication with the wire lumen at the distal end of the projection part, and a first notch that is formed on the more proximal end side than the projection part, and is in communication with the wire lumen. The first notch is formed on a side surface of the shaft, the side surface being positioned on the opposite side of the sensor lumen, and the shaft includes, in a section with the first notch, a bottom portion facing the first notch and a pair of side walls extending to the opposite side of the sensor lumen.

9 Claims, 18 Drawing Sheets

(56)　　　　　　　References Cited

U.S. PATENT DOCUMENTS

2013/0053763 A1 *　2/2013　Makino ............... A61M 25/003
　　　　　　　　　　　　　　　　　　　　　604/523
2021/0060293 A1　　3/2021　Hase et al.

FOREIGN PATENT DOCUMENTS

JP　　　2017-153621　A　　9/2017
JP　　　2017-532104　A　　11/2017
JP　　　 2018-33507　A　　3/2018
JP　　　2020-062079　A　　4/2020
WO　　2016/044211　A1　　3/2016
WO　　2019/189826　A1　　10/2019

* cited by examiner

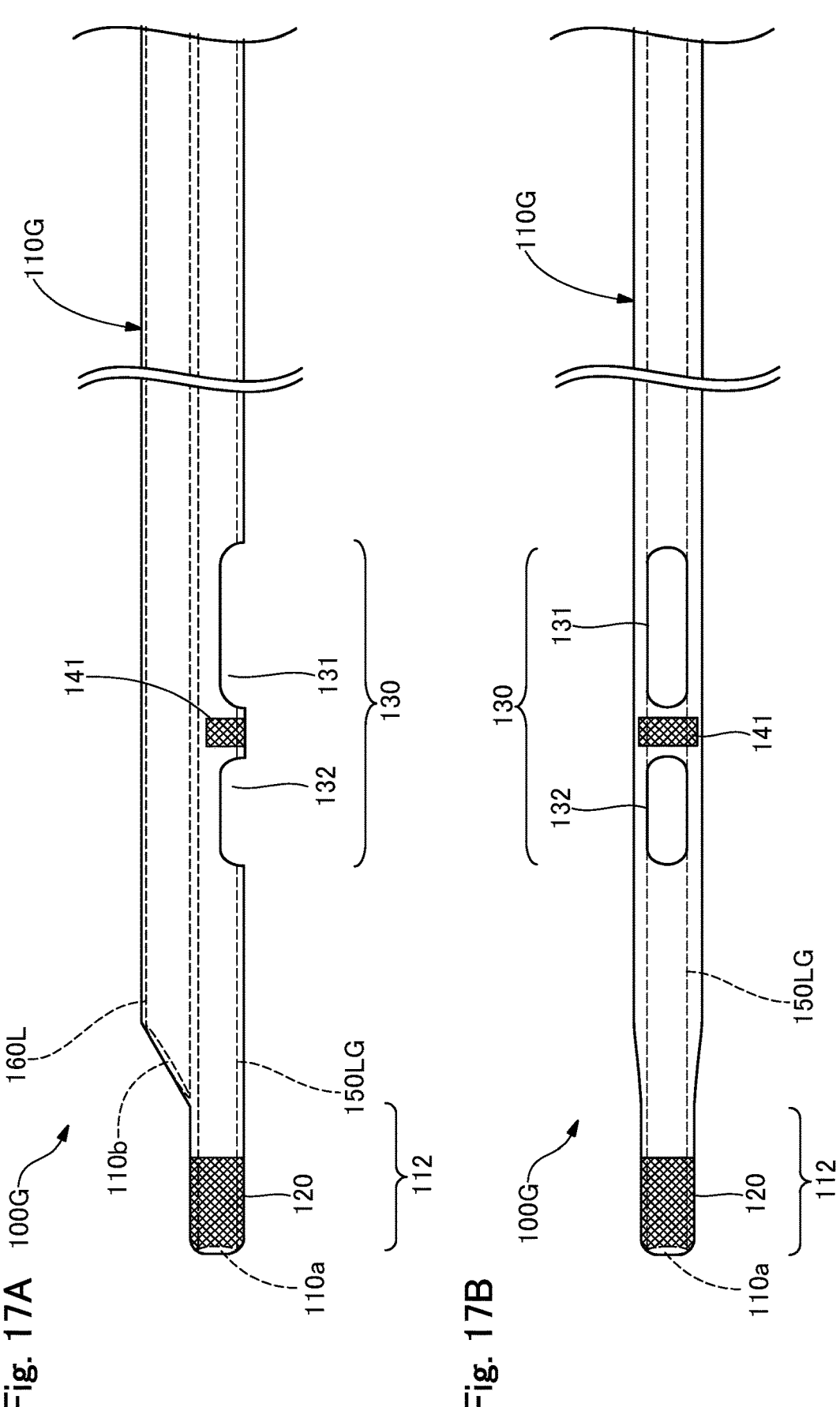

CATHETER

CROSS REFERENCE TO RELATED APPLICATIONS

This application is a continuation application of International Application No. PCT/JP2021/041145, filed Nov. 9, 2021, which claims priority to JP 2021-014792, filed Feb. 2, 2021. The contents of these applications are incorporated herein by reference in their entirety.

TECHNICAL FIELD

This application relates to a catheter.

BACKGROUND

An occlusion may block a blood vessel, such as a Chronic Total Occlusion (CTO). In the procedure of CTO recanalization, a catheter is generally delivered to a position of a CTO lesion using a delivery catheter, and then a penetration guide wire is introduced from a false lumen to a true lumen. Note that the false lumen indicates all dissected lumens formed by medical devices, other than true lumens.

Because of the complicated procedure for CTO recanalization, the procedure performed under sensor guidance (IVUS guide, for example) has been demanded. For example, Patent Literatures 1 to 3 disclose catheters that can be used in the procedure under sensor guidance. The catheters in Patent Literatures 1 to 3 include a sensor lumen (image lumen) and a wire lumen (guide wire lumen) separately, so that a penetration guide wire inserted in the wire lumen can be operated under observation by a sensor inserted in the sensor lumen.

CITATION LIST

Patent Literature

[Patent Literature 1] JP 4065167 B2
[Patent Literature 2] JP 2017-153621 A
[Patent Literature 3] JP 2018-33507 A

SUMMARY

Technical Problem

Here, the diameter of a catheter inserted in a blood vessel is preferably as small as possible. In the catheters described in Patent Literatures 1 and 2, the diameter of the catheter can be reduced because both a delivery guide wire and a penetration guide wire use a single wire lumen. Meanwhile, in the catheters described in Patent Literatures 1 and 2, the wire lumen extending in the longitudinal direction of the catheter includes a first guide wire lumen and a second guide wire lumen, with an area between the first and second guide wire lumens where a guide wire lumen is not present. Therefore, in the catheters described in Patent Literatures 1 and 2, when a delivery guide wire is inserted into the catheter, the delivery guide becomes detached in an area where a guide wire lumen is not present, thus deteriorating usability. Moreover, the catheter described in Patent Literature 3 includes three wire lumens, which improves usability but increases the diameter of the catheter.

Such a problem arises not only in CTO recanalization, but is common to all devices for the procedures performed while different medical devices, such as a delivery guide wire and a penetration guide wire, are exchanged. Moreover, such a problem is also common not only to devices to be inserted into blood vessels, but also to all devices to be inserted into living body lumens, such as the lymph gland system, the biliary system, the urinary tract system, the airway system, the digestive organ system, secretory glands, and reproductive organs.

In order to solve at least a part of the above-described problems, the disclosed embodiments aim at providing a catheter capable of realizing procedures under sensor guidance and performing procedures while different medical devices are exchanged, in which both the reduction in diameter and the improvement of usability are possible.

Solution to the Problem

Disclosed embodiments have been made to solve at least a part of the above-described problems, and can be realized as the following aspects.

(1) According to one aspect of the disclosed embodiments, a catheter with a shaft is provided. In the catheter, the shaft includes a wire lumen extending in a longitudinal direction of the shaft; a sensor lumen that is arranged side by side with the wire lumen; a projection part that includes the wire lumen, projects to the more distal side than the distal end of the sensor lumen, and has a distal end opening communicated to the wire lumen at the distal end of the projection part; and a first notch that is a notch formed on the more proximal end side than the projection part, and is communicated to the wire lumen. The first notch is formed on a side surface of the shaft, the side surface being positioned on the opposite side of the sensor lumen with a center axis of the wire lumen as a reference, and the shaft includes, in a section with the first notch, a bottom portion facing the first notch and a pair of side walls extending from the bottom portion to the opposite side of the sensor lumen.

With this configuration, the shaft of the catheter includes the wire lumen and the sensor lumen arranged side by side with the wire lumen. Thus, it is possible to provide the catheter capable of realizing the procedure under guidance of a sensor (for example, IVUS) inserted in the sensor lumen and performing the procedure, while different medical devices (for example, the delivery guide wire and the penetration guide wire) are exchanged in the wire lumen. Moreover, the distal end opening is formed at the distal end of the projection part, which allows the delivery guide wire to be easily inserted in the wire lumen from this distal end opening. Here, in the section where the first notch is formed, the shaft includes the bottom portion facing the first notch, and the pair of side walls extending from the bottom portion to the opposite side of the sensor lumen. Therefore, when the delivery guide wire in the wire lumen is pushed toward the proximal end side, the side wall provided in the section where the first notch is present supports the delivery guide wire. This suppresses the delivery guide wire from being detached to project to the outside of the shaft. Further, in the side surfaces of the shaft, the side surface positioned on the opposite side of the sensor lumen includes the first notch. This allows the penetration guide wire to easily project to the outside from this first notch. Here, with the side wall provided in the section where the first notch is present, the distal end portion of the penetration guide wire can be pushed out to the outside. Thus, the distal end portion of the penetration guide wire can accurately project to the target tissue. As a result, with this configuration, in the catheter capable of realizing the procedure under guidance of the sensor and performing the procedure while different medical devices are exchanged, both the reduction in diameter and the improvement of usability are possible.

(2) In the catheter of the above-described aspect, the first notch may be elliptical including a first long axis extending along the center axis of the wire lumen and a first short axis extending vertically to the center axis, when the shaft is viewed from the side of the wire lumen, and a length of the first short axis may be equal to an inner diameter of the wire lumen.

With this configuration, the first notch is elliptical, and the length of the first short axis of the first notch is equal to the inner diameter of the wire lumen. Thus, the first notch can be provided in a wide range in the circumferential direction of the wire lumen. Therefore, when the catheter is inserted in the living body lumen, the distal end portion of the penetration guide wire can be easily directed to the target tissue without rotating the catheter even if the position of the first notch of the catheter is separate from the position in the circumferential direction of the target tissue.

(3) In the catheter of the above-described aspect, the shaft may further include a second notch that is a notch formed on the more distal end side or proximal end side than the first notch, and is communicated to the wire lumen, the second notch may be formed on the side surface of the shaft, the side surface being positioned on the same side as the first notch, and the shaft may include, in a section with the second notch, a bottom portion facing the second notch and a pair of side walls extending from the bottom portion to the opposite side of the sensor lumen.

With this configuration, the side surface of the shaft further includes the second notch on the more distal end side or proximal end side than the first notch. This allows the penetration guide wire to project to the outside selectively from either the first notch or the second notch. In the section where the second notch is formed, the shaft includes the bottom portion facing the second notch, and the pair of side walls extending from the bottom portion to the opposite side of the sensor lumen. Thus, when the delivery guide wire in the wire lumen is pushed toward the proximal end side, the side wall provided in the section where the second notch is present supports the delivery guide wire. This suppresses the delivery guide wire from being detached to project to the outside of the shaft. Further, with the side wall provided in the section where the second notch is present, the distal end portion of the penetration guide wire can be pushed out to the outside. Thus, the distal end portion of the penetration guide wire can accurately project to the target tissue.

(4) In the catheter of the above-described aspect, the second notch may be elliptical including a second long axis extending along the center axis of the wire lumen and a second short axis extending vertically to the center axis, when the shaft is viewed from the side of the wire lumen, and a length of the second short axis may be equal to the inner diameter of the wire lumen and a length of the second long axis may be shorter than a length of the first long axis of the first notch.

With this configuration, the second notch is elliptical, and the length of the second short axis of the second notch is equal to the inner diameter of the wire lumen. Thus, the second notch can be provided in a wide range in the circumferential direction of the wire lumen. Therefore, when the catheter is inserted in the living body lumen, the distal end portion of the penetration guide wire can be easily directed to the target tissue without rotating the catheter even if the position of the second notch of the catheter is separate from the position in the circumferential direction of the target tissue. Moreover, the length of the second long axis of the second notch is shorter than the length of the first long axis of the first notch. Thus, the length of the second notch in the longitudinal direction of the shaft can be shorter than the length of the first notch. Therefore, the positioning of the distal end portion of the penetration guide wire relative to the target tissue is easier at the second notch than at the first notch. The operator can selectively use either the first notch or the second notch depending on the position relation between the catheter and a target tissue or a situation such as the size of a target tissue, which further improves usability of the catheter.

(5) In the catheter of the above-described aspect, the shaft further includes, between the distal end and the proximal end of the shaft, the branching lumen branched from the wire lumen, and the branching part formed at the connection portion between the wire lumen and the branching lumen. The distal end side of the branching lumen is connected to the wire lumen, the proximal end side of the branching lumen is positioned on the more proximal end side than the distal end side, the proximal end side of the branching lumen is communicated to the outside through a port formed on a side surface of the shaft, the branching part includes a large diameter portion with an inner diameter of a lumen relatively larger than other parts of the wire lumen, and a boundary wall separating the wire lumen and the branching lumen from each other on the more proximal end side than the large diameter portion.

With this configuration, in the shaft of the catheter, the distal end opening is formed at the distal end of the projection part, which allows the delivery guide wire to be easily inserted in the wire lumen from this distal end opening. Here, the proximal end side of the branching lumen branched from the wire lumen is communicated to the outside through the port formed on the side surface of the shaft. Thus, the proximal end portion of the delivery guide wire in the wire lumen can be pulled out to the outside from the port, which allows the delivery guide wire to be quickly inserted in the catheter. Further, the branching part formed at the connection portion between the wire lumen and the branching part includes the boundary wall separating the wire lumen and the branching lumen from each other. Thus, when the penetration guide wire is inserted in the wire lumen from the proximal end side of the shaft and pushed toward the distal end side of the shaft, the distal end portion of the penetration guide wire is brought into contact with the boundary wall, thus suppressing the distal end portion of the penetration guide wire from advancing toward the branching lumen. As a result, with this configuration, in the catheter capable of realizing the procedure under guidance of the sensor and performing the procedure while different medical devices are exchanged, both the reduction in diameter and the improvement of usability are possible.

(6) In the catheter of the above-described aspect, the port is inclined relative to the center axis of the shaft, and a distal end of the boundary wall may be positioned at the same position as a distal end of the port or on the more distal end side than the distal end of the port in the longitudinal direction of the shaft.

With this configuration, the distal end of the boundary wall is located at the same position as the distal end position of the port or on the more distal end side than the distal end position of the port in the longitudinal direction of the shaft. Thus, when the penetration guide wire is inserted in the wire lumen from the proximal end side of the shaft and pushed toward to the distal end side of the shaft, it is possible to securely suppress the distal end portion of the penetration guide wire from advancing toward the branching lumen.

(7) In the catheter of the above-described aspect, the length in the longitudinal direction of the shaft of the boundary wall may be equal to or longer than the length in the longitudinal direction of the shaft of the port.

With this configuration, the length in the longitudinal direction of the shaft of the boundary wall is equal to or longer than the length in the longitudinal direction of the shaft of the port. Thus, when the penetration guide wire is inserted in the wire lumen from the proximal end side of the shaft and pushed toward the distal end side of the shaft, it is possible to securely suppress the distal end portion of the penetration guide wire from advancing toward the branching lumen.

(8) In the catheter of the above-described aspect, the branching part may further include a raised portion that is raised toward the side of the extending branching lumen, in an area on the more distal end side than the large diameter portion and on the opposite side of the extending branching lumen, in an inner peripheral surface defining the wire lumen.

With this configuration, the branching part further includes the raised portion. Thus, it is possible to guide the wire with the raised portion.

(9) In the catheter of the above-described aspect, in the first case that a wire is inserted to the wire lumen from the distal end opening, a proximal end portion of the wire is brought into contact with the raised portion and thus guided toward the branching lumen, and in the second case that a wire is inserted to the wire lumen from the proximal end side of the shaft, the distal end portion of the wire is brought into contact with the boundary wall to suppress the distal end portion of the wire from advancing toward the branching lumen.

With this configuration, in the first case where the delivery guide wire is inserted to the wire lumen from the distal end opening, the proximal end portion of the delivery guide wire is brought into contact with the raised portion, thereby guiding the proximal end portion of the delivery guide wire toward the branching lumen. In other words, in the first case where the catheter is used as a rapid exchange type (Rx-type), the raised portion guides the proximal end portion of the delivery guide wire toward the branching lumen with the port, thereby improving usability as the Rx-type catheter. Moreover, with the boundary wall of the branching part, in the second case where the penetration guide wire is inserted in the wire lumen from the proximal end side of the shaft, the distal end portion of the penetration guide wire is brought into contact with the boundary wall, thus suppressing the distal end portion of the penetration guide wire from advancing toward the branching lumen. In other words, in the second case where the catheter is used as an over the wire type (OTW-type), the boundary wall guides the distal end portion of the penetration guide wire toward the distal end of the wire lumen, thereby improving usability as the OTW-type catheter. As described above, in the catheter of the first embodiment, the wire lumen can be shared by different medical devices (delivery guide wire, penetration guide wire), which reduces the diameter of the catheter.

The disclosed embodiments can be realized in various aspects such as, for example, a catheter, a manufacturing method or a use method of a catheter, a catheter system including a catheter and other devices such as a sensor, a delivery guide wire, a penetration guide wire, and the like, and a manufacturing method or a use method of a catheter system.

BRIEF DESCRIPTION OF THE DRAWINGS

FIG. 2 is an explanatory view illustrating the configuration of a part on the distal end side of a catheter according to a first embodiment.

FIG. 12 is an explanatory view illustrating the configuration of a part on the distal end side of a catheter according to a third embodiment.

FIG. 13 is an explanatory view illustrating the configuration of a part on the distal end side of a catheter according to a fourth embodiment.

FIG. 14 is an explanatory view illustrating the configuration of a transverse section of a catheter according to a fifth embodiment.

FIG. 15 is an explanatory view illustrating the configuration of a transverse section of a catheter according to a sixth embodiment.

FIGS. 17A and 17B are explanatory views illustrating the configuration of a part on the distal end side of a catheter according to an eighth embodiment.

DETAILED DESCRIPTION

First Embodiment

Figure 1:
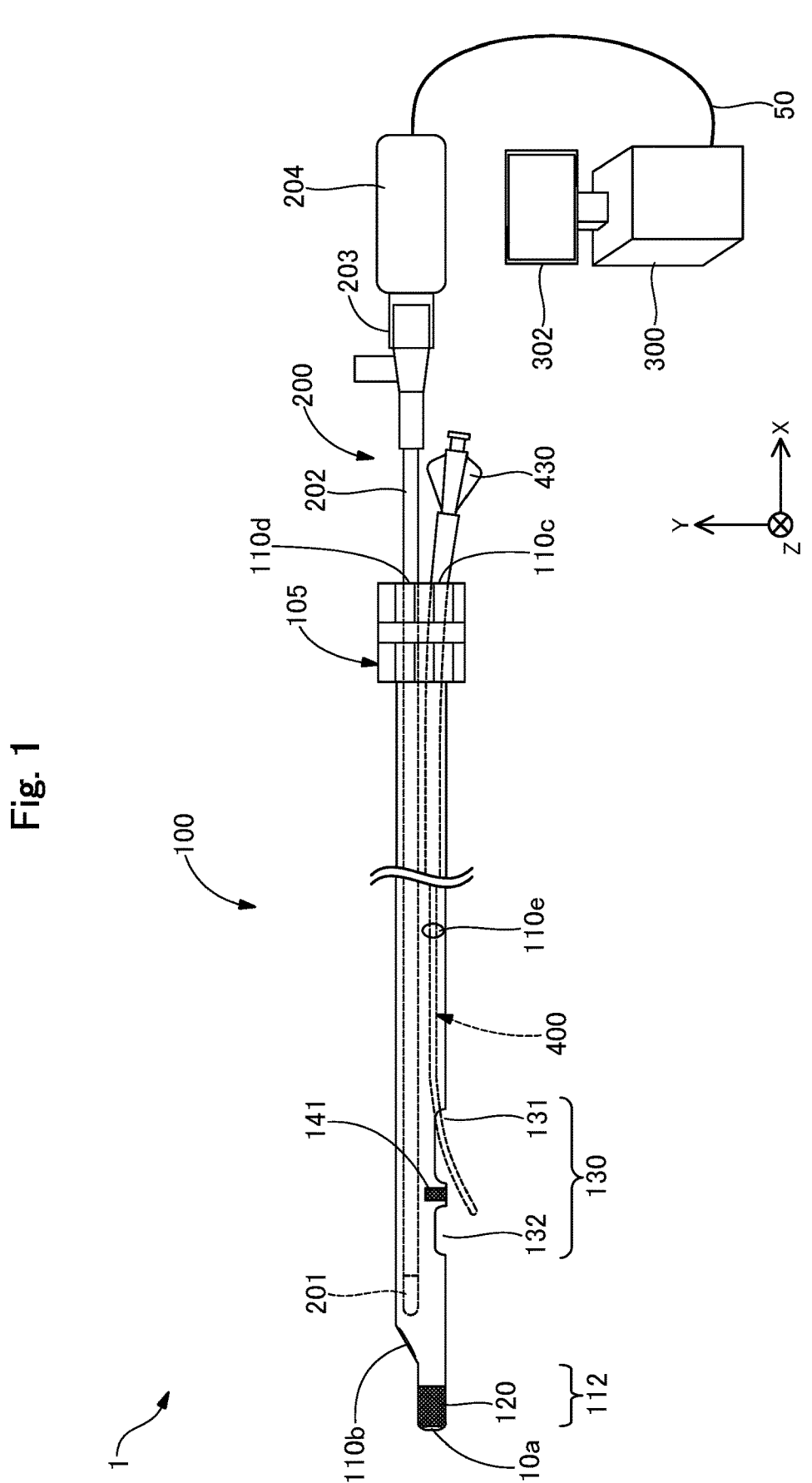
FIG. 1 is an explanatory view illustrating the configuration of a recanalization catheter system.

FIG. 1 is an explanatory view illustrating the configuration of a recanalization catheter system 1. The recanalization catheter system 1 is used for therapeutics of a chronic total occlusion (CTO) occurred in a blood vessel with antegrade approach. The recanalization catheter system 1 includes a catheter 100, an imaging sensor 200, an imaging console 300, and a penetration guide wire 400. FIG. 1 illustrates a schematic side view of the catheter 100, and illustrates, with broken lines, each of a part on the distal end side of the imaging sensor 200 and a part on the distal end side of the penetration guide wire 400 that are inserted in the catheter 100.

In FIG. 1, the relative ratio of the sizes of the components is partially different from the actual ratio, for convenience of description. Moreover, FIG. 1 partially illustrates the components in an exaggerated manner. Further, FIG. 1 illustrates XYZ axes that are orthogonal to each other. The X-axis corresponds to the longitudinal direction of the catheter 100, the Y-axis corresponds to the height direction of the catheter 100, and the Z-axis corresponds to the width direction of the catheter 100. The left side (–X-axis direction) of FIG. 1 is referred to as the "distal end side" of the catheter 100 and that of each component, while the right side (+X-axis direction) of FIG. 1 is referred to as the "proximal end side" of the catheter 100 and that of each component. Moreover, in both ends in the longitudinal direction (X-axis direction) of the catheter 100 and those of each component, one end positioned on the distal end side is referred to as a "distal end", and the other end positioned on the proximal end side is referred to as a "proximal end". Further, the distal end and the vicinity thereof are referred to as a "distal end portion", and the proximal end and the vicinity thereof are referred to as a "proximal end portion". The distal end side is inserted into a living body, and the proximal end side is operated by an operator such as a doctor. These points are also common to the figures following FIG. 1.

Figure 2:
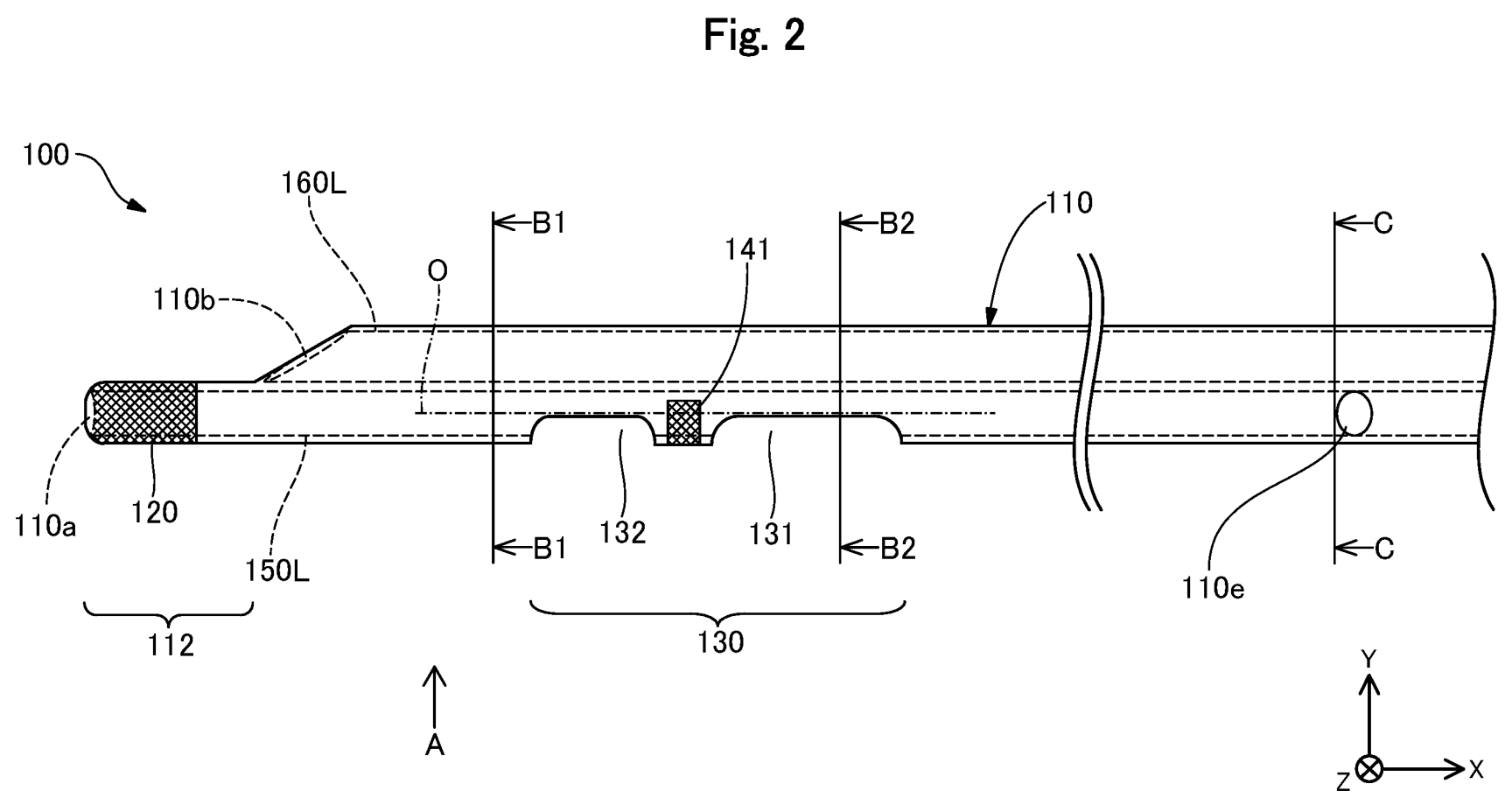
Figure 3:
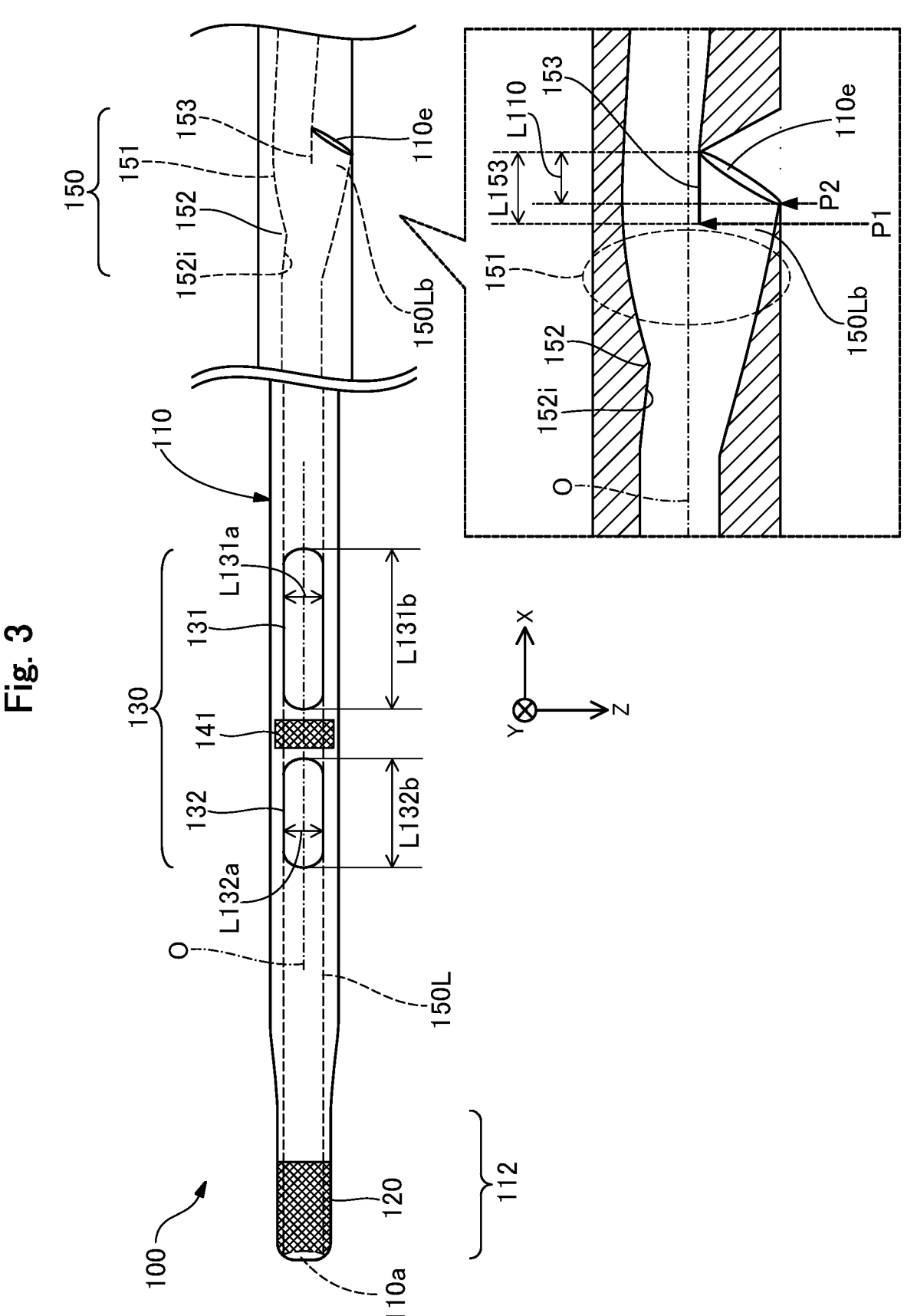
FIG. 3 is an explanatory view illustrating the configuration of the catheter viewed from an A direction in FIG. 2.

FIG. 2 is an explanatory view illustrating the configuration of a part on the distal end side of the catheter 100. FIG. 3 is an explanatory view illustrating the configuration of the catheter 100 viewed from the A direction in FIG. 2. FIG. 3 illustrates, in a balloon in the lower stage thereof, an enlarged sectional view of the vicinity of a branching part 150. FIG. 2 and FIG. 3 illustrate, in the upper stage thereof, a wire lumen 150L and a sensor lumen 160L formed in the catheter 100, with broken lines. Further, FIG. 2 and FIG. 3 partially illustrate, with a dashed line, a center axis O of the wire lumen 150L.

Figure 4A:
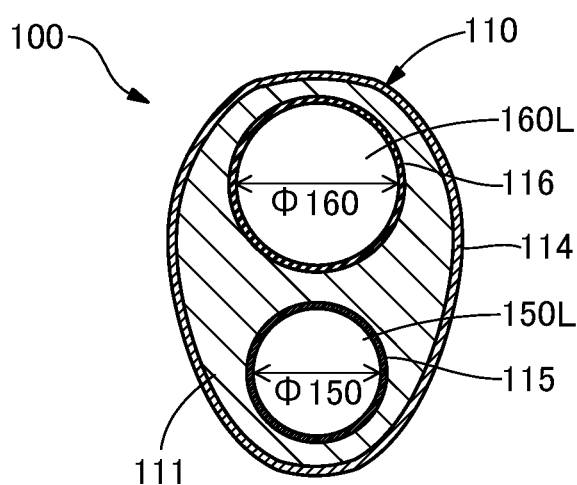
FIGS. 4A and 4B are explanatory views illustrating the configuration of a transverse section of the catheter.
Figure 4B:
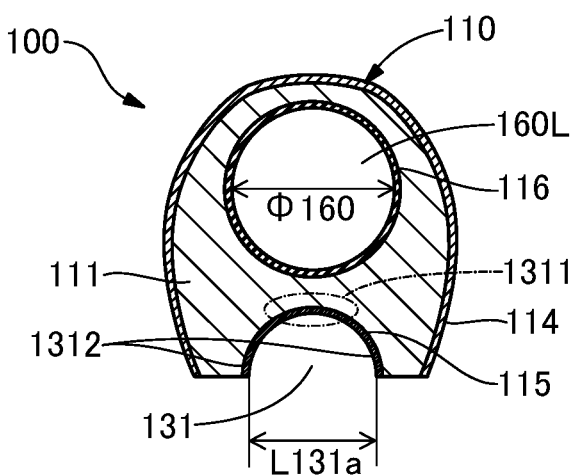
Figure 5:
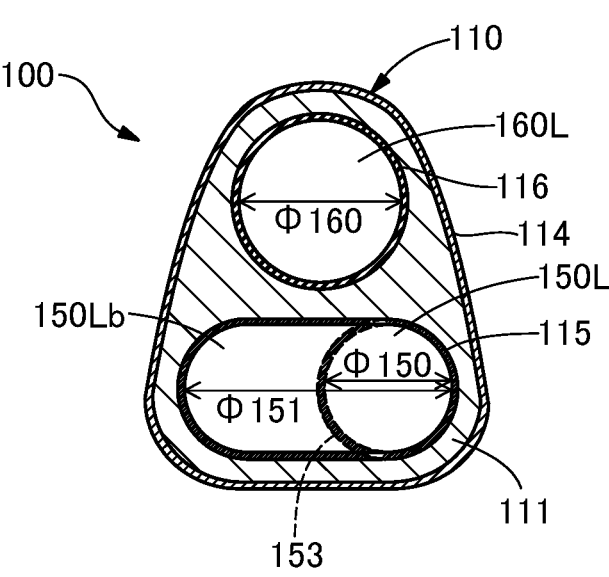
FIG. 5 is an explanatory view illustrating the configuration of a transverse section of the catheter.

FIGS. 4A and 4B, and FIG. 5 are explanatory views illustrating the configuration of a transverse section of the catheter 100. FIG. 4A is a transverse sectional view of the catheter 100 along B1-B1 line of FIG. 2. FIG. 4B is a transverse sectional view of the catheter 100 along B2-B2 line of FIG. 2. FIG. 5 is a transverse sectional view of the catheter 100 along C-C line of FIG. 2. The following describes the configuration of the catheter 100 with reference to FIG. 1 to FIG. 5. FIG. 2 to FIG. 5 do not illustrate the imaging sensor 200 and the penetration guide wire 400.

As illustrated in FIG. 1, the catheter 100 includes a shaft 110 and an adjusting device 105. As illustrated in FIG. 2 and FIG. 3, the shaft 110 includes the wire lumen 150L, the sensor lumen 160 L, a projection part 112, a notch part 130, and the branching part 150 (FIG. 3).

As illustrated in FIG. 2, the wire lumen 150L and the sensor lumen 160L are lumens each extending in the longitudinal direction (X-axis direction) of the shaft 110. Inside the shaft 110, the wire lumen 150L and the sensor lumen 160L are arranged side by side to be parallel to each other.

The sensor lumen 160L extends linearly from the distal end to the proximal end of the shaft 110. Meanwhile, as illustrated in FIG. 3, the wire lumen 150L is branched to two directions at a position between the distal end and the proximal end of the shaft 110 (for example, an arbitrary position about 200 mm to 400 mm from the distal end). One of them extends substantially linearly to the proximal end of the shaft 110, and the other is communicated to the outside through a port 110e formed on a side surface of the shaft 110. In the following, the lumen branched from the wire lumen 150L and connected to the port 110e is also referred to as a "branching lumen 150Lb". Moreover, in the shaft 110, the vicinity of the connection portion between the wire lumen 150L and the branching lumen 150Lb is also referred to as a "branching part 150". The details of the branching part 150 and the branching lumen 150Lb are described later.

As illustrated in FIG. 2, a part on the distal end side of the wire lumen 150L is positioned on the more distal end side (–X-axis side) than the distal end of the sensor lumen 160L. In the following, a part surrounding this part on the distal end side of the wire lumen 150L in the shaft 110 is also referred to as a "projection part 112". Note that the lengths in the X-axis direction of the wire lumen 150L and the sensor lumen 160L can be arbitrarily determined as long as the wire lumen 150L is longer than the sensor lumen 160L.

The projection part 112 is a part of the shaft 110 projecting to the more distal end side than the distal end of the sensor lumen 160L, as described above, and includes therein a part on the distal end side of the wire lumen 150L. A distal tip 120 is jointed to a part on the distal end side of the projection part 112 so as to surround the projection part 112. The distal tip 120 is a substantially cylindrical member with an R provided to the distal end portion thereof. Note that the distal tip 120 may have an arbitrary shape, and may have a substantially truncated cone shape with the outer diameter reduced from the proximal end side to the distal end side, for example. The distal tip 120 may be colored to improve the visibility, and may be formed of a radiopaque material. To joint the distal tip 120 and the shaft 110, there may be adopted jointing of resin by hot melting or jointing with an insulating adhesive such as an epoxy-based adhesive.

In the shaft 110, a distal end first opening 110a connecting the wire lumen 150L and the outside is provided at a position corresponding to the distal end of the wire lumen 150L (in other words, the distal end of the projection part 112). The distal end first opening 110a corresponds to a "distal end opening". In the shaft 110, a proximal end first opening 110c connecting the wire lumen 150L and the outside is provided at a position corresponding to the proximal end of the wire lumen 150L (FIG. 1). Further, in the shaft 110, a distal end second opening 110b connecting the sensor lumen 160L and the outside is provided at a position corresponding to the distal end of the sensor lumen 160L. In the shaft 110, a proximal end second opening 110d connecting the sensor lumen 160L and the outside is provided at a position corresponding to the proximal end of the sensor lumen 160L (FIG. 1).

Here, in the catheter 100 of the embodiment, the distal end second opening 110b is positioned on the more proximal end side than the distal end first opening 110a. Moreover, the distal end second opening 110b is inclined relative to the longitudinal direction (X-axis direction) of the shaft 110. The distal end second opening 110b is an opening for discharging liquid introduced into the sensor lumen 160L from the proximal end second opening 110d. Thus, the distal end second opening 110b may be vertical relative to the longitudinal direction of the shaft 110. Moreover, the distal end second opening 110b may not be provided at a position corresponding to the distal end of the sensor lumen 160L, as long as it is provided at a position connecting a part of the vicinity of the distal end portion of the sensor lumen 160L and the outside.

As illustrated in FIG. 4A, the shaft 110 includes an outer shaft 114, a first inner shaft 115, a second inner shaft 116, and a sealing member 111.

The outer shaft 114, the first inner shaft 115, and the second inner shaft 116 all have a hollow elongated shape. The outer shaft 114 has a substantially elliptical transverse section. The first inner shaft 115 and the second inner shaft 116 have a substantially circular transverse section. The first inner shaft 115 and the second inner shaft 116 are inserted in the lumen of the outer shaft 114, and extend in substantially parallel to each other along the longitudinal direction of the outer shaft 114. The lumen of the first inner shaft 115 functions as the above-described wire lumen 150L. Meanwhile, the lumen of the second inner shaft 116 functions as the above-described sensor lumen 160L. As illustrated in FIG. 4A, the inner diameter $\Phi150$ of the first inner shaft 115 (inner diameter of wire lumen 150L) is smaller than the inner diameter $\Phi160$ of the second inner shaft 116 (inner diameter of sensor lumen 160L). Note that the inner diameters $\Phi150$ and $\Phi160$ can be determined arbitrarily.

The sealing member 111 seals (fixes) the first inner shaft 115 and the second inner shaft 116 in the outer shaft 114. The sealing member 111 is arranged inside the outer shaft 114 and outside the first inner shaft 115 and the second inner shaft 116. To joint the outer shaft 114, the first inner shaft 115, the second inner shaft 116, and the sealing member 111, there may be adopted jointing of resin by hot melting or jointing with an insulating adhesive such as an epoxy-based adhesive.

As illustrated in FIG. 2, the notch part 130 is a notch formed in the shaft 110 on the more proximal end side than the projection part 112, the notch connecting the wire lumen 150L and the outside. In the embodiment, the notch part 130 includes two notches (first notch 131, second notch 132).

The first notch 131 is formed on a side surface of the shaft 110, the side surface being positioned on the opposite side of the sensor lumen 160L with the center axis O of the wire lumen 150L as a reference. As illustrated in FIG. 3, the first notch 131 is elliptical including a long axis (hereinafter, also referred to as a "first long axis") extending along the center axis O of the wire lumen 150L and a short axis (hereinafter, also referred to as a "first short axis") extending vertically to the center axis O, when the shaft 110 is viewed from the side of the wire lumen 150L. As illustrated in FIG. 3, and FIGS. 4A and 4B, a length L131a of the first short axis of the first notch 131 is equal to the inner diameter $\Phi150$ of the wire lumen 150L. Note that the expression "equal" in the embodiment indicates "almost same", and allows a tolerance for manufacturing error or the like.

As illustrated in FIG. 4B, the shaft 110 includes, in the section where the first notch 131 is formed, a bottom portion 1311 and a pair of side walls 1312. In the shaft 110, the bottom portion 1311 is a part facing the first notch 131. In the shaft 110, the side wall 1312 is a part extending from the bottom portion 1311 to the opposite side of the sensor lumen 160L. In other words, the shaft 110 includes, in the section where the first notch 131 is formed, a substantially semicircular groove surrounded by the bottom portion 1311 and the side walls 1312.

As illustrated in FIG. 2, the second notch 132 is provided on the more distal end side than the first notch 131. The second notch 132 is formed on a side surface of the shaft 110, the side surface being on the same side as the first notch 131 (that is, the side surface positioned on the opposite side of the sensor lumen 160L with the center axis O of the wire lumen 150L as a reference). As illustrated in FIG. 3, the second notch 132 is elliptical including a long axis (hereinafter, also referred to as a "second long axis") extending along the center axis O of the wire lumen 150L and a short axis (hereinafter, also referred to as a "second short axis") extending vertically to the center axis O, when the shaft 110 is viewed from the side of the wire lumen 150L. A length L132a of the second short axis of the second notch 132 is equal to the inner diameter $\Phi150$ of the wire lumen 150L. The shaft 110 includes, in the section where the second notch 132 is formed, a bottom portion facing the second notch 132, and a pair of side walls extending from the bottom portion to the opposite side of the sensor lumen 160L. The details are the same as those of the first notch 131.

As illustrated in FIG. 3, a length L132b of the second long axis of the second notch 132 is shorter than a length L131b of the first long axis of the first notch 131. Thus, as illustrated in FIG. 3, the area of the elliptical shape of the second notch 132 is smaller than the area of the elliptical shape of the first notch 131, when the shaft 110 is viewed from the side of the wire lumen 150L. Note that the length L132b of the second axis of the second notch 132 indicates a length between the end on the distal end side and the end on the most proximal end side of the elliptical shape of the second notch part 132, when the shaft 110 is viewed from the side of the wire lumen 150L (viewpoint in FIG. 3). This also applies to the length L131b of the first long axis of the first notch 131.

As illustrated in FIG. 2 and FIG. 3, a marker 141 is jointed between the first notch 131 and the second notch 132 on the outer peripheral surface of the shaft 110. The marker 141 is a semicircular member along the outer peripheral surface of the shaft 110. The marker 141 may be colored to improve the visibility, and may be formed of a radiopaque material. To joint the marker 141 and the shaft 110, there may be adopted jointing of resin by hot melting or jointing with an insulating adhesive such as an epoxy-based adhesive.

Note that in the example of the embodiment, the second notch 132 is provided on the more distal end side than the first notch 131. However, the second notch 132 may be provided on the more proximal end side (FIGS. 2 and 3: +X-axis direction) than the first notch 131. Moreover, the marker 141 may be omitted.

As illustrate in the lower stage of FIG. 3, the distal end side of the branching lumen 150Lb is connected to the wire lumen 150L. The proximal end side of the branching lumen 150Lb is positioned on the more proximal end side of the shaft 110 than the distal end side. The proximal end side of the branching lumen 150Lb is communicated to the outside through the port 110e formed on the side surface of the shaft 110. In other words, the port 110e as an opening connecting the branching lumen 150Lb and the outside is provided at a position corresponding to the proximal end of branching lumen 150Lb in the shaft 110. The branching lumen 150Lb extends in a direction separate from the wire lumen 150L toward the proximal end side from the distal end side of the shaft 110.

The branching part 150 includes a large diameter portion 151, a raised portion 152, and a boundary wall 153. The large diameter portion 151 (lower stage in FIG. 3: circle with a broken line) is a part where the inner diameter of the lumen is relatively larger than that of other parts of the wire lumen 150L. As illustrated in FIG. 5, the inner diameter $\Phi151$ of the lumen in the large diameter portion 151 is larger than the inner diameter $\Phi150$ of the wire lumen 150L. Note that in the large diameter portion 151, the inner diameter in the longitudinal direction of the substantially elliptical lumen is referred to as an "inner diameter $\Phi151$ of the lumen". For convenience of description, FIG. 5 illustrates, with a dashed line, the boundary wall 153 not apparent on the C-C section.

As illustrated in the lower stage of FIG. 3, the raised portion 152 is a portion, in the inner peripheral surface of the branching part 150, where a part of an inner peripheral surface 152i defining the wire lumen 150L is raised. In the inner peripheral surface 152i of the branching part 150, the raised portion 152 is provided in an area on the more distal end side than the large diameter portion 151 and on the opposite side of the side where the branching lumen 150Lb extends. In the raised portion 152, the inner peripheral surface 152i of the branching part 150 is raised to the side where the branching lumen 150Lb extends. As illustrated in the lower stage of FIG. 3, the raised portion 152 of the embodiment has a shape smoothly raised from the inner peripheral surface 152i of the branching part 150. The length in the longitudinal direction (X-axis direction) of the shaft 110 of the raised portion 152 may be determined arbitrarily.

The boundary wall 153 is a part of the shaft 110 provided on the more proximal end side than the large diameter portion 151, the part separating the wire lumen 150L and the branching lumen 150Lb from each other. As illustrated in FIG. 5, the boundary wall 153 of the embodiment has a curved plate shape. However, the boundary 153 may have an arbitrary shape such as a plate shape or a pinnate shape as long as it separates the wire lumen 150L and the branching lumen 150Lb from each other. As illustrated in the lower stage of FIG. 3, a distal end P1 of the boundary wall 153 is positioned on the more distal end side than a distal end P2 of the port 110e in the longitudinal direction (X-axis direction) of the shaft 110. Note that the distal end P1 of the boundary 153 may be at the same position as the distal end P2 of the port 110e. In the embodiment, the expression "same" indicates "almost same", and allows a difference due to a manufacturing error or the like. The length L153 in the X-axis direction of the boundary wall 153 is equal to or longer than the length L110 in the X-axis direction of the port 110e. Here, the port 110e is inclined relative to the center axis O of the shaft 110. Thus, the length L110 in the X-axis direction of the port 110e indicates a length measured when the port 110e is projected on the X axis, as illustrated in the lower stage of FIG. 3.

Figures 6A, 6B:
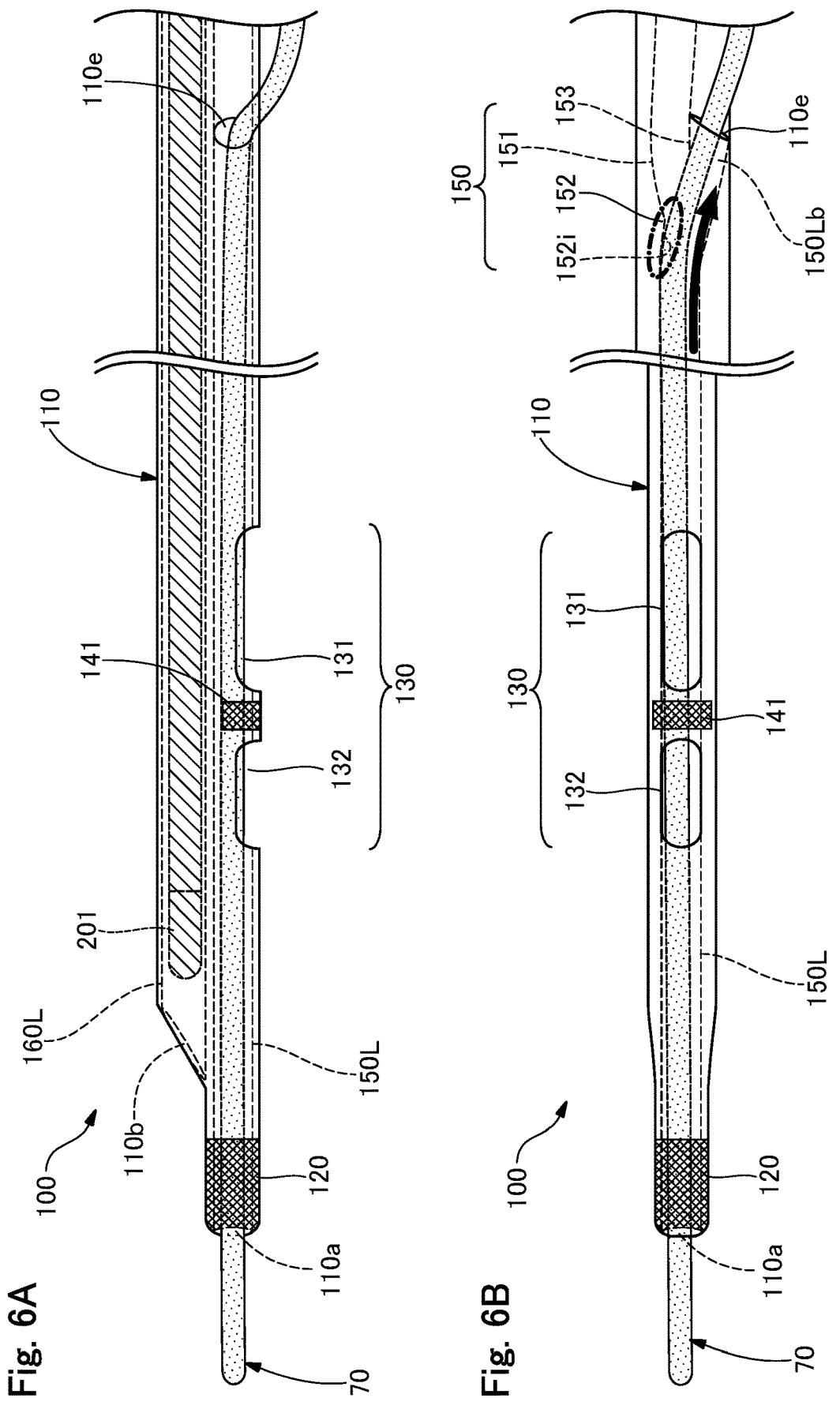
FIGS. 6A and 6B are diagrams for explaining an action of a raised portion in a first case.

FIGS. 6A and 6B are diagrams for explaining an action of the raised portion 152 in the first case. FIG. 6A illustrates a side view of the catheter 100 viewed from the same direction as FIG. 2, and FIG. 6B illustrates a bottom view of the catheter 100 viewed from the same direction as FIG. 3. Note that FIGS. 6A and 6B illustrate a delivery guide wire 70, as an example of the wire, with dot hatching. The "first case" indicates a case where the delivery guide wire 70 is inserted to the wire lumen 150L from the distal end first opening 110a and advances in the wire lumen 150L from the distal end side toward the proximal end side. In other words, the first case is a case where the catheter 100 is used as a rapid exchange type (Rx-type) catheter.

In the first case, an operator inserts the proximal end portion of the delivery guide wire 70 to the wire lumen 150L from the distal end first opening 110a, and pulls it out to the outside from the port 110e through the branching lumen 150Lb. Here, as illustrated in FIG. 6B, the proximal end portion of the delivery guide wire 70 comes into contact with the raised portion 152, thereby automatically advancing toward the side of the branching lumen 150Lb (direction of a bold arrow) and being guided to the outside from the port 110e at the proximal end of the branching lumen 150Lb.

Figures 7A, 7B:
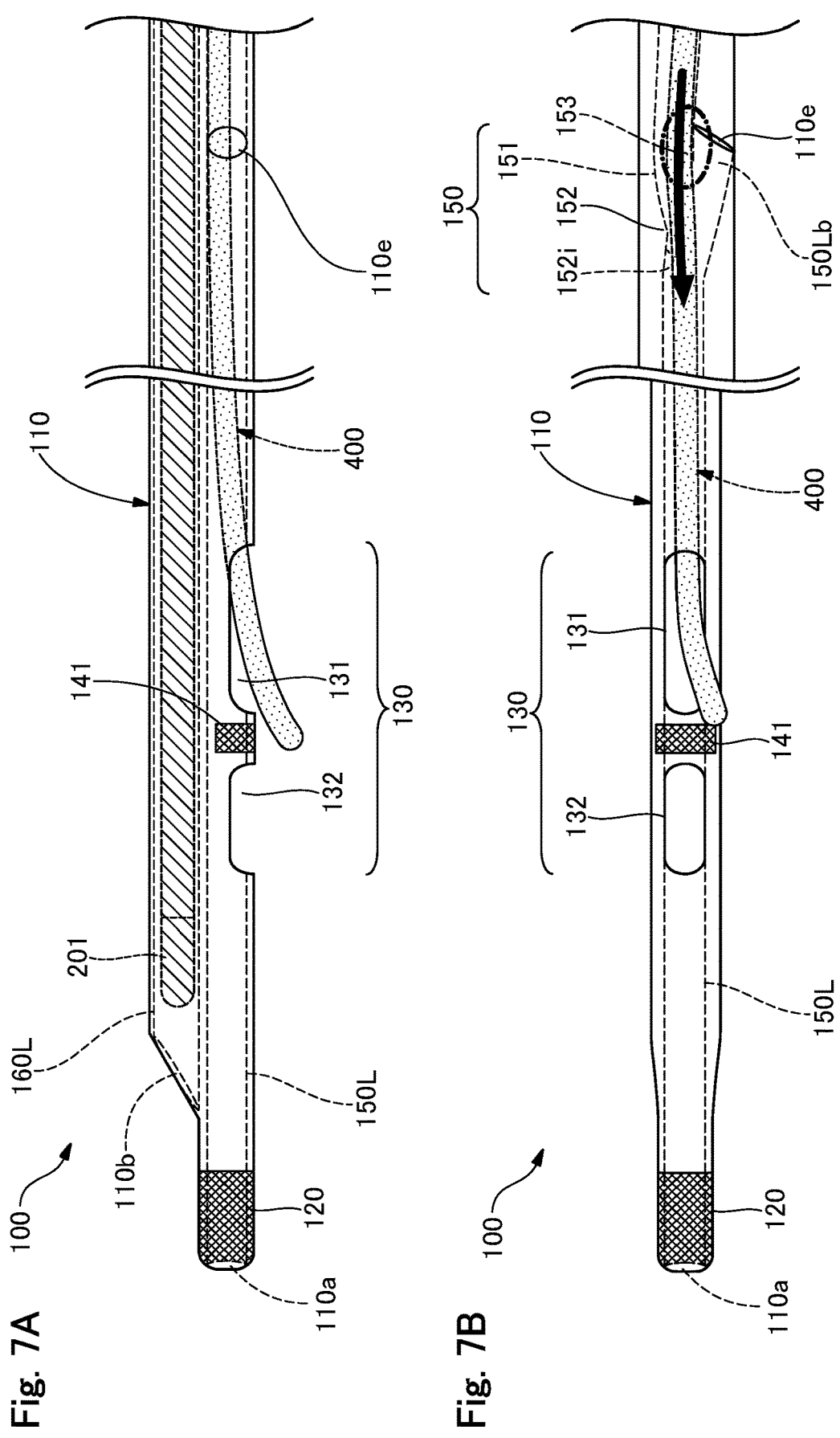
FIGS. 7A and 7B are diagrams for explaining an action of a boundary wall in a second case.

FIGS. 7A and 7B are diagrams for explaining an action of the boundary wall 153 in the second case. FIG. 7A illustrates a side view of the catheter 100 viewed from the same direction as FIG. 2, and FIG. 7B illustrates a bottom view of the catheter 100 viewed from the same direction as FIG. 3. Note that FIGS. 7A and 7B illustrate the penetration guide wire 400, as an example of the wire, with dot hatching. The "second case" indicates a case where the penetration guide wire 400 is inserted to the wire lumen 150L from the proximal end first opening 110c and advances in the wire lumen 150L from the proximal end side toward the distal end side. In other words, the second case is a case where the catheter 100 is used as an over the wire type (OTW-type) catheter.

In the second case, an operator inserts the distal end portion of the penetration guide wire 400 to the wire lumen 150L from the distal end second opening 110b so that it advances in the branching part 150 (without letting the penetration guide wire 400 wrongly enter the branching lumen 150Lb), and pulls it out to the outside from the first notch 131 or the second notch 132. Here, as illustrated in FIG. 7B, the distal end portion of the penetration guide wire 400 comes into contact with the boundary wall 153, thereby automatically advancing straight in the branching part 150 (in the bold arrow direction) while being suppressed from advancing toward the branching lumen 150Lb, and reaches the part where the first notch 131 or the second notch 132 is provided.

Returning to FIG. 1, the description is continued. The adjusting device 105 is an operation part for moving the imaging sensor 200 in the sensor lumen 160L forward and backward. The adjusting device 105 includes a dial operable by an operator. With the rotation of the dial, the imaging sensor 200 inserted in the sensor lumen 160L is moved forward or backward.

The outer shaft 114, the first inner shaft 115, the second inner shaft 116, the sealing member 111, and the adjusting device 105 may be formed of known materials including, for example, nylon resin such as polyamide, polyolefins such as polyethylene, polypropylene, and ethylene-propylene copolymers, polyesters such as polyethylene terephthalate, thermoplastic resin such as polyvinyl chloride, ethylene-vinyl acetate copolymers, crosslinked ethylene-vinyl acetate copolymers, and polyurethanes, polyamide elastomer, polyolefin elastomer, polyurethane elastomer, silicone rubber, latex rubber, or the like. The outer shaft 114, the first inner shaft 115, the second inner shaft 116, the sealing member 111, and the adjusting device 105 may be formed of the same material, or at least some of them or all of them may be formed of a different material from the other components. Note that in the outer shaft 114, the first inner shaft 115, the second inner shaft 116, and the sealing member 111, at least a part positioned in the vicinity of the notch part 130 (first notch 131 and second notch 132) is preferably formed of resin having a small difference in acoustic impedance from the living tissue, such as polyethylene, for example. This is not to inhibit ultrasonic waves emitted to the living tissue from the imaging sensor 200.

The distal tip 120 and the marker 141 are formed of a flexible resin material such as a polyurethane elastomer, for example. The distal tip 120 and the marker 141 may be formed of a radiopaque resin material or metal material. In the case of using a radiopaque resin material, for example, a radiopaque material such as bismuth trioxide, tungsten, or barium sulfate is mixed to polyamide resin, polyolefin resin, polyester resin, polyurethane resin, silicone resin, fluororesin, or the like. In the case of using a radiopaque metals, for example, gold, platinum, tungsten, an alloy containing these elements (for example, a platinum-nickel alloy) can be used. The distal tip 120 and the marker 141 may be formed of the same material or different materials.

Figure 8:
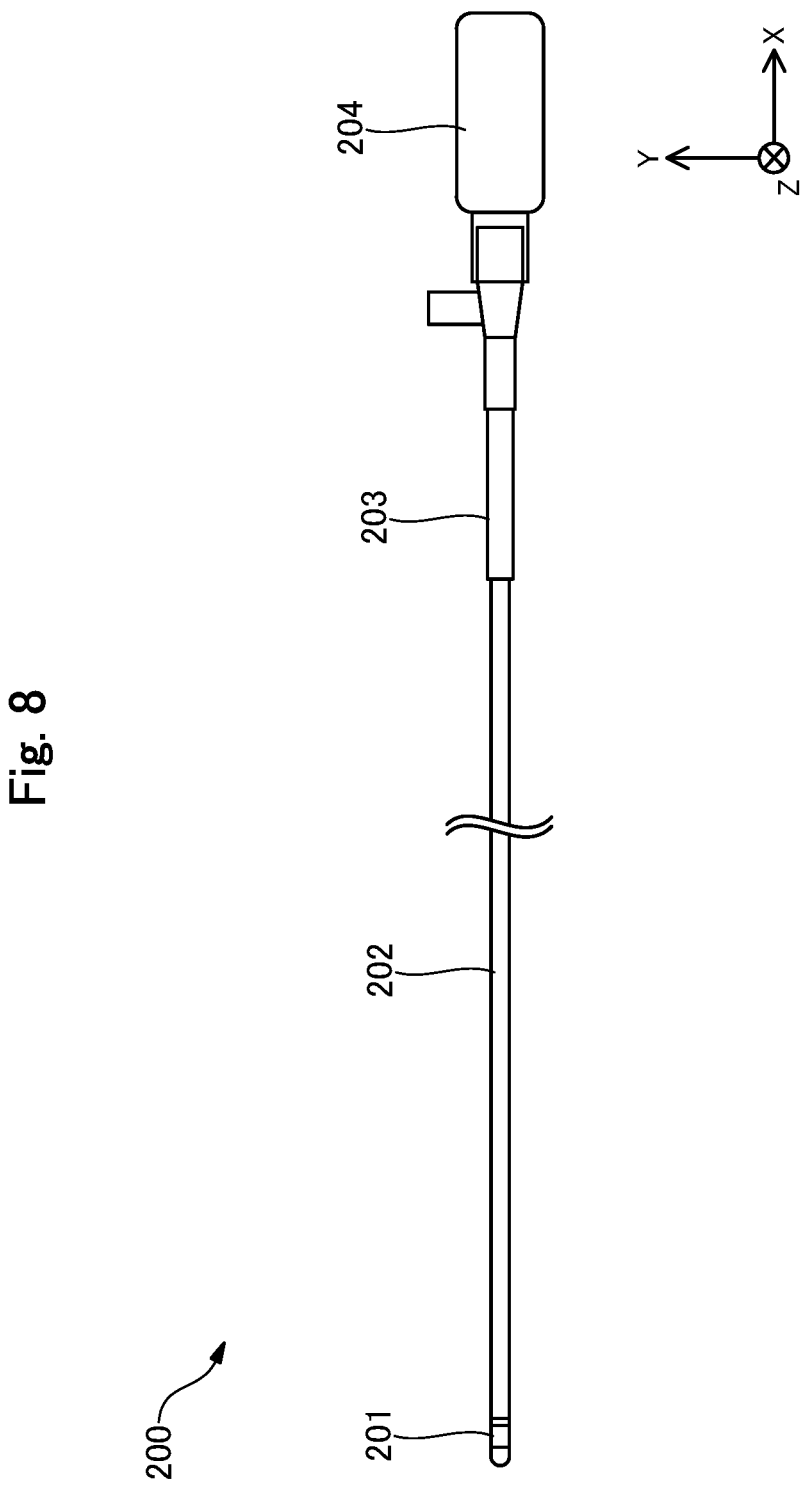
FIG. 8 is a schematic view of an imaging sensor.

FIG. 8 is a schematic view of the imaging sensor 200. The imaging sensor 200 is a "sensor" with an elongated shape that acquires the information of a living tissue. The imaging sensor 200 includes a transducer 201, a driving cable 202, and a connector 203. The transducer 201 includes an ultrasonic probe (also referred to as an ultrasonic vibrator, a piezoelectric body, an ultrasonic transmitting/receiving element, or an ultrasonic element) that emits ultrasonic waves to a living tissue and receives ultrasonic waves reflected during propagation in the living tissue. The driving cable 202 includes therein a coaxial cable electrically connecting the transducer 201 and the motor drive 204. The connector 203 connects the coaxial cable of the driving cable 202 and the motor drive 204 controlling the rotation of the transducer 201. Note that the motor drive 204 is electrically connected to the imaging console 300 by a cable 50.

The imaging console 300 illustrated in FIG. 1 controls the imaging sensor 200, generates an image, and displays the image. To be more specific, in accordance with the operation of the adjusting device 105, the imaging console 300 moves the transducer 202 in the sensor lumen 160L in the longitudinal direction of the shaft 110 (X-axis direction) or rotates the transducer 201 in the circumferential direction of the shaft 110 (YZ-axis direction). Moreover, in accordance with the operation by an operator using an input means (not illustrated), the imaging console 300 controls the transducer 201 to emit ultrasonic waves and receive reflected waves. The reflected waves received by the transducer 201 are transmitted to the imaging console 300 through the driving cable 202 and the cable 50. The imaging console 300 generates an image (two-dimensional image) with tone gradation in accordance with the intensity of the received reflected waves, and displays the generated image on a display 302. In the following, the image acquired by the imaging sensor 200 and displayed on the display 302 is also referred to as a "sensor image".

The penetration guide wire 400 illustrated in FIG. 1 is an elongated medical device including a pointed portion at the distal end thereof. The pointed portion is a portion having an arrowhead shape or a wedge shape from the proximal end side toward the distal end side. With the pointed portion provided at the distal end, the penetration guide wire 400 can penetrate the living tissue. The penetration guide wire 400 corresponds to "a guide wire penetrating a living tissue".

FIGS. 9A and 9B, and FIGS. 10A and 10B are diagrams for explaining a use method of the recanalization catheter system 1. FIGS. 9A and 9B, and FIGS. 10A and 10B each illustrates a coronary artery 80 as an example of a living body lumen, a CTO 81 occurred in the coronary artery 80, a false lumen 82 formed in the intima or under the intima of the coronary artery 80 (all dissected lumens formed by the delivery guide wire 70, other than true lumens), a true lumen 84, a fibrotic film or a plaque 83 (hereinafter, also referred to as a "fibrotic film" 83) present between the false lumen 82 and the true lumen 84. Note that the fibrotic film 83 may be formed in a fiber form on the surface of a CTO lesion.

Figures 9A, 9B:
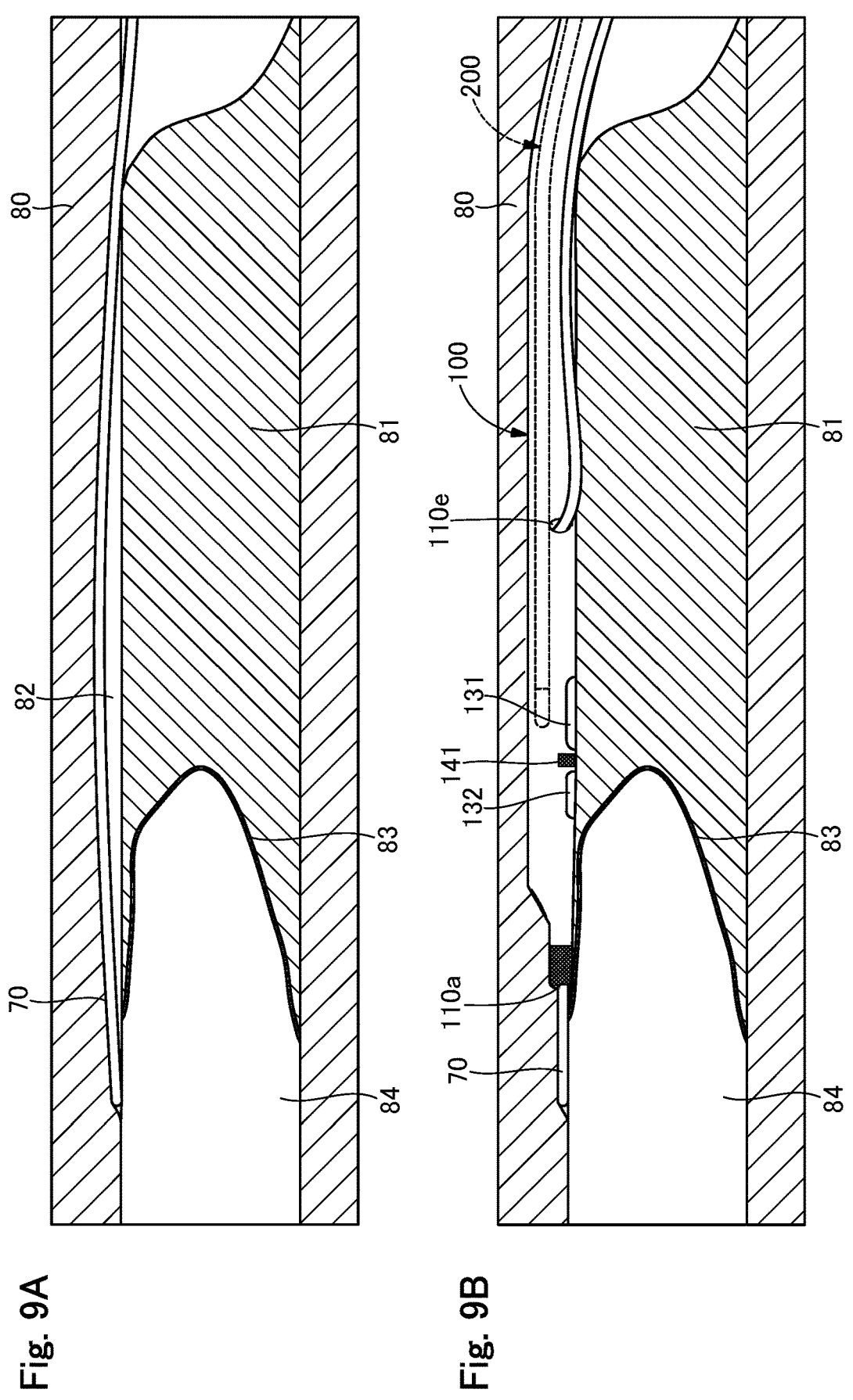
FIGS. 9A and 9B are diagrams for explaining a use method of the recanalization catheter system.

FIG. 9A illustrates the coronary artery 80 in which delivery guide wire 70 is inserted. In FIG. 9A, the delivery guide wire 70 operated by an operator wrongly enters an intima of the coronary artery 80, or forms the false lumen 82 below the intima.

FIG. 9B illustrates a situation in which the catheter 100 is delivered using the delivery guide wire 70. The operator performs the operation described in FIGS. 6A and 6B to insert the delivery guide wire 70 to the catheter 100. As described in FIGS. 6A and 6B, in the catheter 100 of the embodiment, the raised portion 152 guides the proximal end portion of the delivery guide wire 70 to the branching lumen 150Lb where the port 110e is provided. Thus, it is possible to easily pull out the proximal end portion of the delivery guide wire 70 to the outside from the port 110e. Moreover, the catheter 100 of the embodiment shortens a feeding distance of the delivery guide wire 70 in the wire lumen 150L, as compared with the conventional case where the delivery guide wire 70 is pulled out from the proximal end first opening 110c (FIG. 1) on the proximal end side. As a result, it is possible to reduce time required for inserting the delivery guide wire 70 to the catheter 100. Thereafter, the operator delivers the catheter 100 to the false lumen 82 along the delivery guide wire 70, as illustrated in FIG. 9B.

Figures 10A, 10B:
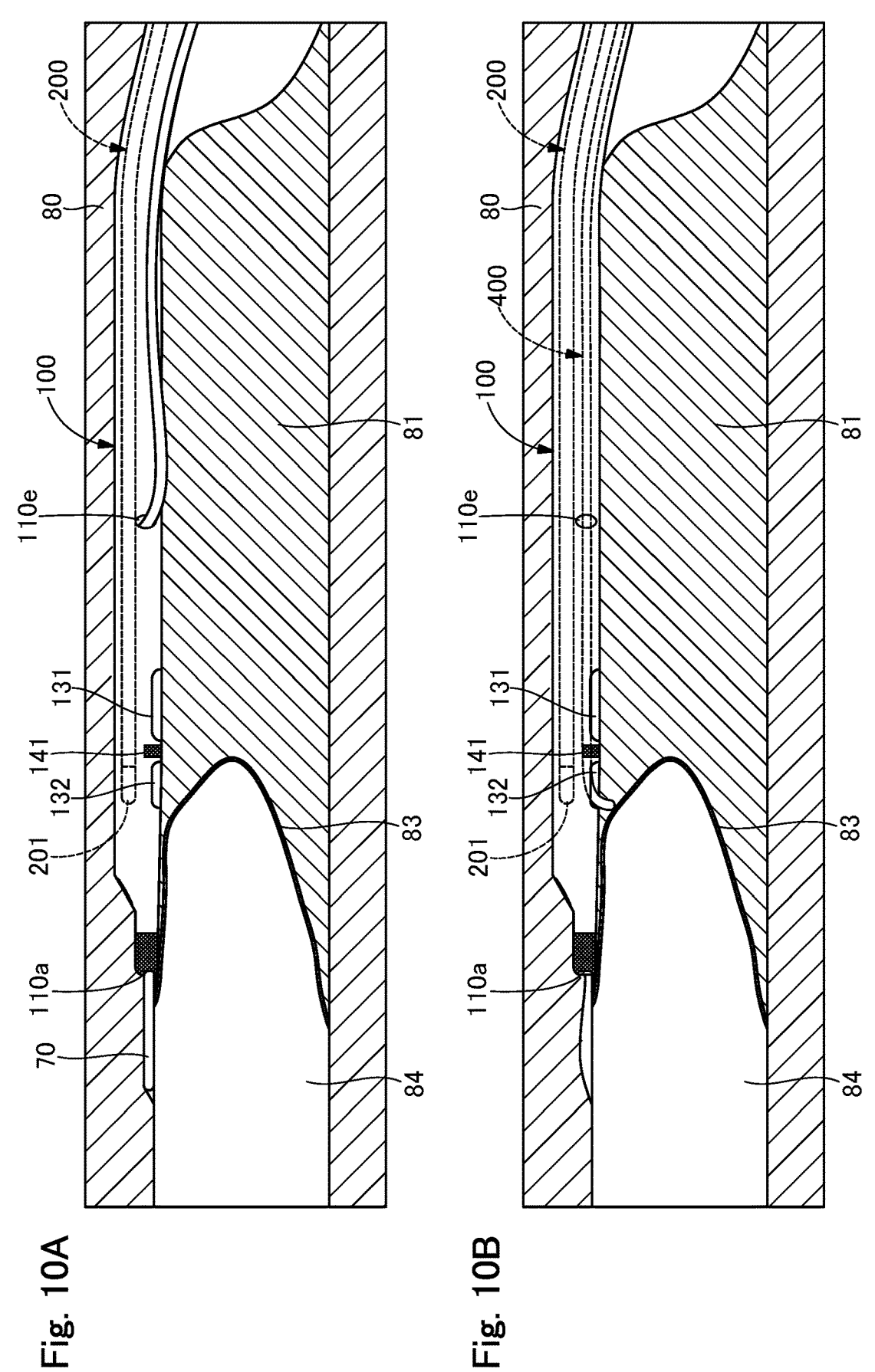
FIGS. 10A and 10B are diagrams for explaining a use method of the recanalization catheter system.

FIG. 10A illustrates a situation where the positions of the catheter 100 and the imaging sensor 200 are adjusted. The operator adjusts each of the positions described in the following a1 to a3. Note that the adjustment a2 may be omitted.

(a1) Adjustment of the position in the longitudinal direction (FIG. 1: X-axis direction) of the catheter 100. The operator moves the catheter 100 along the coronary artery 80 so that the first notch 131 and the second notch 132 of the catheter 100 are arranged at the positions optimate for the penetration guide wire 400 to penetrate the true lumen 84. The adjustment a1 can be performed while the position of the coronary artery 80 on the sensor image or the position of the marker 141 on the X-axis image is confirmed.

(a2) Adjustment of the position in the circumferential direction (FIG. 1: YZ-axis direction) of the catheter 100. The operator rotates the catheter 100 in the circumferential direction so that the catheter 100 directs as illustrated in the drawing (that is, the direction where the first notch 131 and the second notch 132 are positioned on the side of the CTO 81). The adjustment a2 can be performed while the position relation between the delivery guide wire 70 and the coronary artery 80 on the sensor image is confirmed.

(a3) Adjustment of the position in the longitudinal direction (FIG. 1: X-axis direction) of the transducer 201 of the imaging sensor 200. The operator operates the adjusting device 105 to move the transducer 201 so that the transducer 201 is arranged at a position adequate for observing the penetration of the penetration guide wire 400. The adjustment a3 can be performed while the coronary artery 80 on the sensor image is confirmed.

FIG. 10B illustrates a situation in which the penetration guide wire 400 penetrates a living tissue. First, the operator removes the delivery guide wire 70. Here, in the catheter 100 of the embodiment, the length of the delivery guide wire 70 inserted in the wire lumen 150L is shorter than the conventional case described in FIG. 8B, which allows the delivery guide wire 70 to be removed more easily than the conventional case.

After removing the delivery guide wire 70, the operator performs the operation described in FIGS. 7A and 7B to insert the penetration guide wire 400 to the catheter 100. As described in FIGS. 7A and 7B, in the catheter 100 of the embodiment, the boundary wall 153 suppresses the distal end portion of the penetration guide wire 400 from wrongly entering the branching lumen 150Lb. Therefore, the distal end portion of the penetration guide wire 400 can smoothly project from the first notch 131 or the second notch 132. Then, the operator guides the pointed portion of the penetration guide wire 400 to the above-described optimal position for penetration while confirming the distal end of the penetration guide wire 400 on the sensor image. Thereafter, the pointed portion of the penetration guide wire 400 penetrates a living tissue (target tissue), so that the distal end of the penetration guide wire 400 reaches the true lumen 84.

Such a method enables recanalization of the CTO 81 in the recanalization catheter system 1. Note that the above-described method is merely an example, and the recanalization catheter system 1 can be used in various procedures. For example, the recanalization catheter system 1 may be used not only for the approach from the false lumen 82 to the true lumen 84 but also for the approach to penetrate a CTO from the true lumen 84 on the near side to the true lumen 84 on the far side.

Effect Example 1

As described above, in the catheter 100 of the first embodiment, the shaft 110 includes the wire lumen 150L and the sensor lumen 160L arranged side by side with the wire lumen 150L. Thus, it is possible to provide the catheter 100 capable of realizing the procedure under guidance of the imaging sensor 200 (for example, IVUS) inserted in the sensor lumen 160L and performing the procedure while different medical devices (for example, the delivery guide wire 70 and the penetration guide wire 400) are exchanged in the wire lumen 150L (FIGS. 9A and 9B, FIGS. 10A and 10B). Moreover, the distal end first opening 110*a* is formed at the distal end of the projection part 112, which allows the delivery guide wire 70 to be easily inserted in the wire lumen 150L from this distal end first opening 110*a* (FIG. 6A). Here, in the section where the first notch 131 is formed, the shaft 110 includes the bottom portion 1311 facing the first notch 131, and the pair of side walls 1312 extending from the bottom portion 1311 to the opposite side of the sensor lumen 160L (FIG. 4B). Thus, when the delivery guide wire 70 in the wire lumen 150L is pushed toward the proximal end side, the side wall 1312 provided in the section where the first notch 131 is present supports the delivery guide wire 70. This suppresses the delivery guide wire 70 from being detached to project to the outside of the shaft 110. Further, in the side surfaces of the shaft 110, the side surface positioned on the opposite side of the sensor lumen 160L includes the first notch 131. This allows the penetration guide wire 400 to easily project to the outside from this first notch 131 (FIG. 7A). Here, using the side wall 1312 provided in the section where the first notch 131 is present, the distal end portion of the penetration guide wire 400 can be pushed out to the outside. Thus, the distal end portion of the penetration guide wire 400 can accurately project to the living tissue (target tissue). As a result, the catheter 100 of the first embodiment is the catheter 100 capable of realizing the procedure under guidance of the imaging sensor 200 and performing the procedure while different medical devices are exchanged, in which both the reduction in diameter and the improvement of usability are possible.

Moreover, in the catheter 100 of the first embodiment, the first notch 131 is elliptical, and the length L131*a* of the first short axis of the first notch 131 is equal to the inner diameter φ150 of the wire lumen 150L. Thus, the first notch 131 can be provided in a wide range in the circumferential direction of the wire lumen 150L (FIG. 3). Therefore, when the catheter 100 is inserted in the living body lumen, the distal end portion of the penetration guide wire 400 can be easily directed to the target tissue without rotating the catheter 100 even if the position of the first notch 131 of the catheter 100 is separate from the position in the circumferential direction of the living tissue (target tissue). Consequently, in the catheter 100 of the first embodiment, the above-described adjustment a2, for example, may be omitted.

Moreover, in the catheter 100 of the first embodiment, the side surface of the shaft 110 further includes the second notch 132 on the more distal end side or proximal end side than the first notch 131 (FIG. 2, FIG. 3). Therefore, the penetration guide wire 400 can project to the outside selectively from either the first notch 131 or the second notch 132. In the section where the second notch 132 is formed, the shaft 110 includes the bottom portion facing the second notch 132, and the pair of side walls extending from the bottom portion to the opposite side of the sensor lumen. Thus, when the delivery guide wire 70 in the wire lumen 150L is pushed toward the proximal end side, the side wall provided in the section where the second notch 132 is present supports the delivery guide wire 70. This suppresses the delivery guide wire 70 from being detached to project to the outside of the shaft 110. Further, using the side wall provided in the section where the second notch 132 is present, the distal end portion of the penetration guide wire 400 can be pushed out to the outside. Thus, the distal end portion of the penetration guide wire 400 can accurately project to the living tissue (target tissue).

Moreover, in the catheter 100 of the first embodiment, the second notch 132 is elliptical, and the length of the second short axis L132*a* of the second notch 132 is equal to the inner diameter of the wire lumen 150L. Thus, the second notch 132 can be provided in a wide range in the circumferential direction of the wire lumen 150L (FIG. 3). Therefore, when the catheter 100 is inserted in the living body lumen, the distal end portion of the penetration guide wire 400 can be easily directed to the target tissue without rotating the catheter 100 even if the position of the second notch 132 of the catheter 100 is separate from the position in the circumferential direction of the living tissue (target tissue). Moreover, the length L132*b* of the second long axis of the second notch 132 is shorter than the length L131*b* of the first long axis of the first notch 131. Thus, the length of the second notch 132 in the longitudinal direction of the shaft 110 can be shorter than the length of the first notch 131 (FIG. 3). Therefore, the positioning of the distal end portion of the penetration guide wire 400 relative to the target tissue is easier at the second notch 132 than at the first notch 131. The operator can selectively use either the first notch 131 or the second notch 132 depending on the position relation between the catheter 100 and a target tissue or a situation such as the size of a target tissue, which further improves usability of the catheter 100.

Effect Example 2

As described above, in the catheter 100 of the first embodiment, the shaft 110 includes the distal end first opening 110*a* at the distal end of the projection part 112, which allows the delivery guide wire 70 to be easily inserted in the wire lumen 150L from this distal end first opening 110*a* (FIG. 6A). Here, the proximal end side of the branching lumen 150Lb branched from the wire lumen 150L is communicated to the outside through the port 110*e* formed on the side surface of the shaft 110. Thus, the proximal end portion of the delivery guide wire 70 in the wire lumen 150L can be pulled out to the outside from the port 110*e*, which allows the delivery guide wire 70 to be quickly inserted in the catheter 100 (FIG. 6A). Further, the branching part 150 formed at the connection portion between the wire lumen 150L and the branching part 150Lb includes the boundary wall 153 separating the wire lumen 150L and the branching lumen 150Lb from each other (FIG. 5). Thus, when the penetration guide wire 400 is inserted in the wire lumen 150L from the proximal end side of the shaft 110 and pushed toward the distal end side of the shaft 110, the distal end portion of the penetration guide wire 400 is brought into contact with the boundary wall 153, thus suppressing the distal end portion of the penetration guide wire 400 from advancing toward the branching lumen 150Lb (FIG. 7B). As a result, the catheter 100 of the first embodiment is the catheter 100 capable of realizing the procedure under guidance of the imaging sensor 200 and performing the procedure while different medical devices are exchanged, in which both the reduction in diameter and the improvement of usability are possible.

Further, in the catheter 100 of the first embodiment, the distal end P1 of the boundary wall 153 is located at the same position as the distal end position P2 of the port 110e, or on the more distal end side than the distal end position P2 of the port 110e (lower stage in FIG. 3). Thus, when the penetration guide wire 400 is inserted in the wire lumen 150L from the proximal end side of the shaft 110 and pushed toward the distal end side of the shaft 110, it is possible to securely suppress the distal end portion of the penetration guide wire 400 from advancing toward the branching lumen 150Lb.

Further, in the catheter 100 of the first embodiment, the length L153 in the longitudinal direction of the shaft 110 of the boundary wall 153 is equal to or longer than the length L110 in the longitudinal direction of the shaft 110 of the port 110e (lower stage in FIG. 3). Thus, when the penetration guide wire 400 is inserted in the wire lumen 150L from the proximal end side of the shaft 110 and pushed toward the distal end side of the shaft 110, it is possible to securely suppress the distal end portion of the penetration guide wire 400 from advancing toward the branching lumen 150Lb.

Further, in the catheter 100 of the first embodiment, the branching part 150 further includes the raised portion 152. Thus, it is possible to guide the delivery guide wire 70 with the raised portion 152. To be more specific, in the first case where the delivery guide wire 70 is inserted to the wire lumen 150L from the distal end first opening 110a, the proximal end portion of the delivery guide wire 70 is brought into contact with the raised portion 152, thereby guiding the proximal end portion of the delivery guide wire 70 toward the branching lumen 150Lb (FIG. 6B). In other words, in the first case where the catheter 100 is used as an Rx-type, the raised portion 152 guides the proximal end portion of the delivery guide wire 70 toward the branching lumen 150Lb with the port 110e, thereby improving usability as the Rx-type catheter 100.

Moreover, with the boundary wall 153 of the branching part 150, in the second case where the penetration guide wire 400 is inserted in the wire lumen 150L from the proximal end side of the shaft 110, the distal end portion of the penetration guide wire 400 is brought into contact with the boundary wall 153, thus suppressing the distal end portion of the penetration guide wire 400 from advancing toward the branching lumen 150Lb (FIG. 7B). In other words, in the second case where the catheter 100 is used as an OTW-type, the boundary wall 153 guides the distal end portion of the penetration guide wire 400 toward the distal end of the wire lumen 150L, thereby improving usability as the OTW-type catheter 100. As described above, in the catheter 100 of the first embodiment, the wire lumen 150L can be shared by different medical devices (delivery guide wire 70, penetration guide wire 400), which reduces the diameter of the catheter 100.

Second Embodiment

Figure 11:
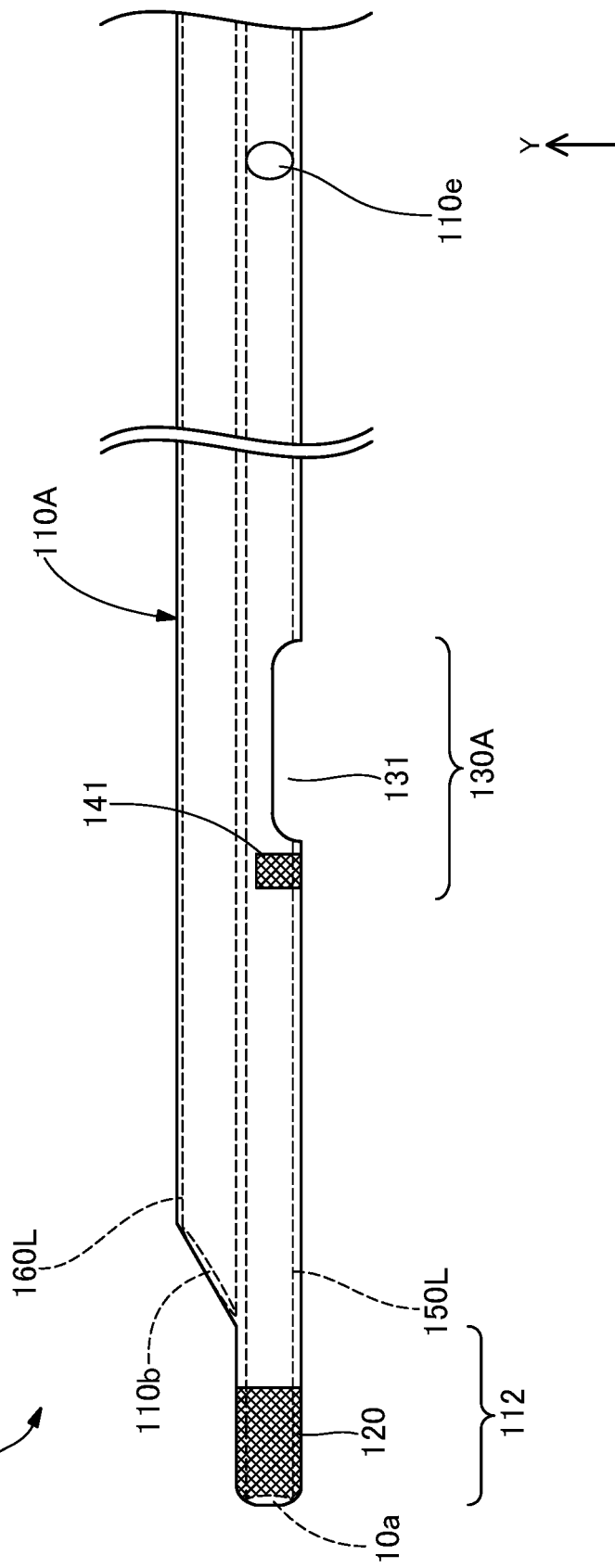
FIG. 11 is an explanatory view illustrating the configuration of a part on the distal end side of a catheter according to a second embodiment.

FIG. 11 is an explanatory view illustrating the configuration of a part on the distal end side of a catheter 100A according to the second embodiment. The recanalization catheter system 1 of the second embodiment includes the catheter 100A illustrated in FIG. 11 instead of the catheter 100 described in the first embodiment. A shaft 110A of the catheter 100A includes a notch part 130A instead of the notch part 130. The notch part 130A does not include the second notch 132 described in the first embodiment, and includes only the single first notch 131.

In this manner, the configuration of the notch part 130A can be changed variously, and the notch part 130A may be formed only by the single first notch 131. Here, the marker 141 may be arranged on the more distal end side than the first notch 131, or may be arranged on the more proximal end side than the first notch 131. Such a catheter 100A of the second embodiment can also exert similar effects as in the above-described first embodiment.

Third Embodiment

Figure 12:
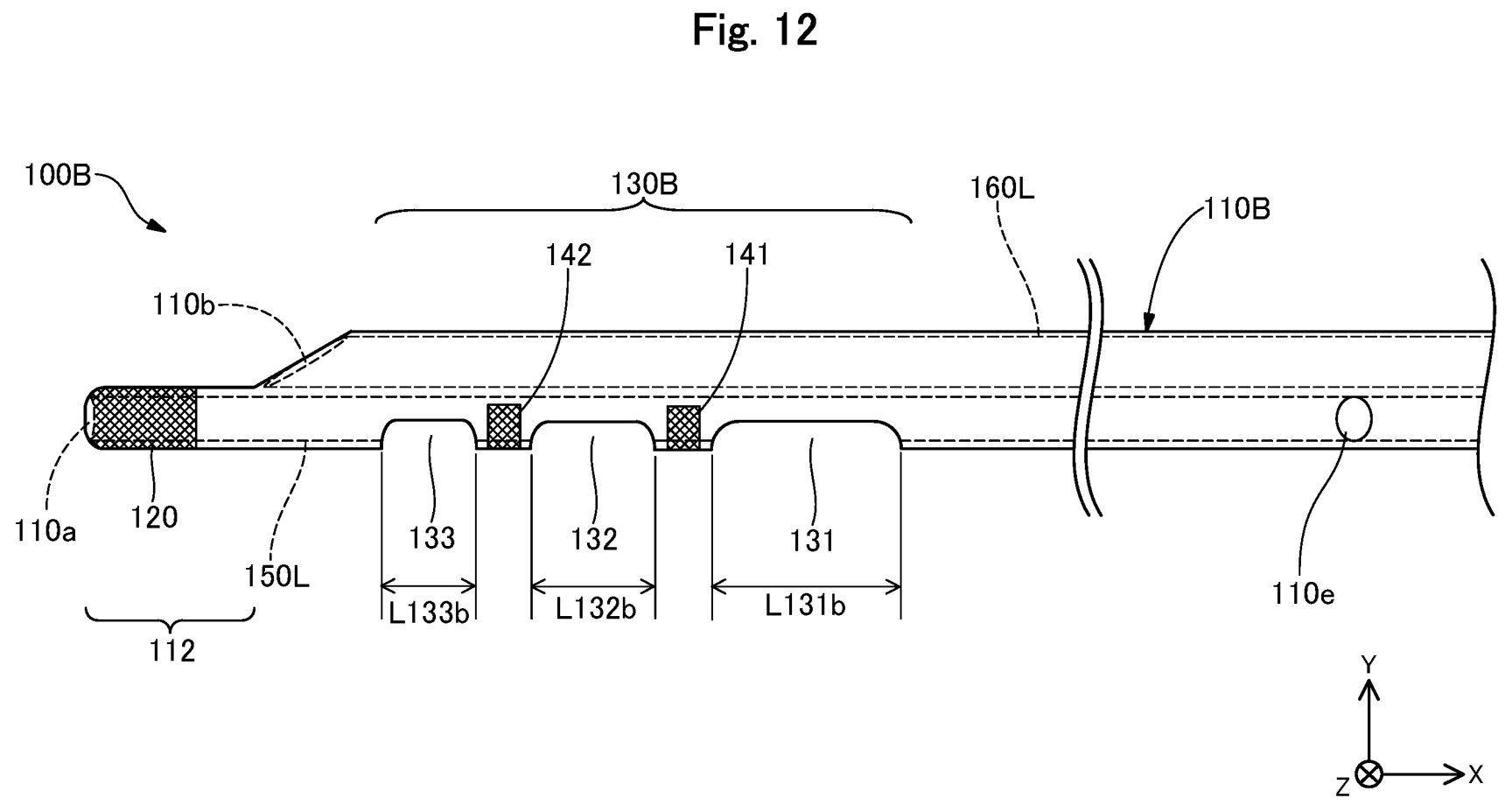

FIG. 12 is an explanatory view illustrating the configuration of a part on the distal end side of a catheter 100B according to the third embodiment. The recanalization catheter system 1 of the third embodiment includes the catheter 100B illustrated in FIG. 12 instead of the catheter 100 described in the first embodiment. A shaft 110B of the catheter 100B includes a notch part 130B instead of the notch part 130. The notch part 130 further includes a third notch 133 in addition to the first notch 131 and the second notch 132 that are described in the first embodiment.

The third notch 133 is provided on the more distal end side than the second notch 132. In the side surfaces of the shaft 110B, the third notch 133 is formed on the side surface on the same side as the first notch 131. When the shaft 110B is viewed from the side of the wire lumen 150L, the third notch 133 is elliptical including a long axis and a short axis. The length of the short axis of the third notch 133 is equal to the inner diameter ɸ150 of the wire lumen 150L. The length L133b of the long axis of the third notch 133 is shorter than the length L131b of the first long axis of the first notch 131, and is shorter than the length L132b of the second long axis of the second notch 132. In the section where the third notch 133 is formed, the shaft 110B includes a bottom portion facing the third notch 133, and a pair of side walls extending from the bottom portion to the opposite side of the sensor lumen 160L.

A second marker 142 is jointed between the second notch 132 and the third notch 133 on the outer peripheral surface of the shaft 110B. The second marker 142 is a semicircular member along the outer peripheral surface of the shaft 110B. Similarly to the marker 141 described in the first embodiment, the second marker 142 may be colored to improve the visibility, and may be formed of a radiopaque material.

In this manner, the configuration of the notch part 130B can be changed variously, and the notch part 130B may be formed by three or more notches (first notch 131, second notch 132, third notch 133). Moreover, the third notch 133 may be provided on the more proximal end side than the first notch 131. Such a catheter 100B of the third embodiment can also exert similar effects as in the above-described first embodiment.

Fourth Embodiment

Figure 13:
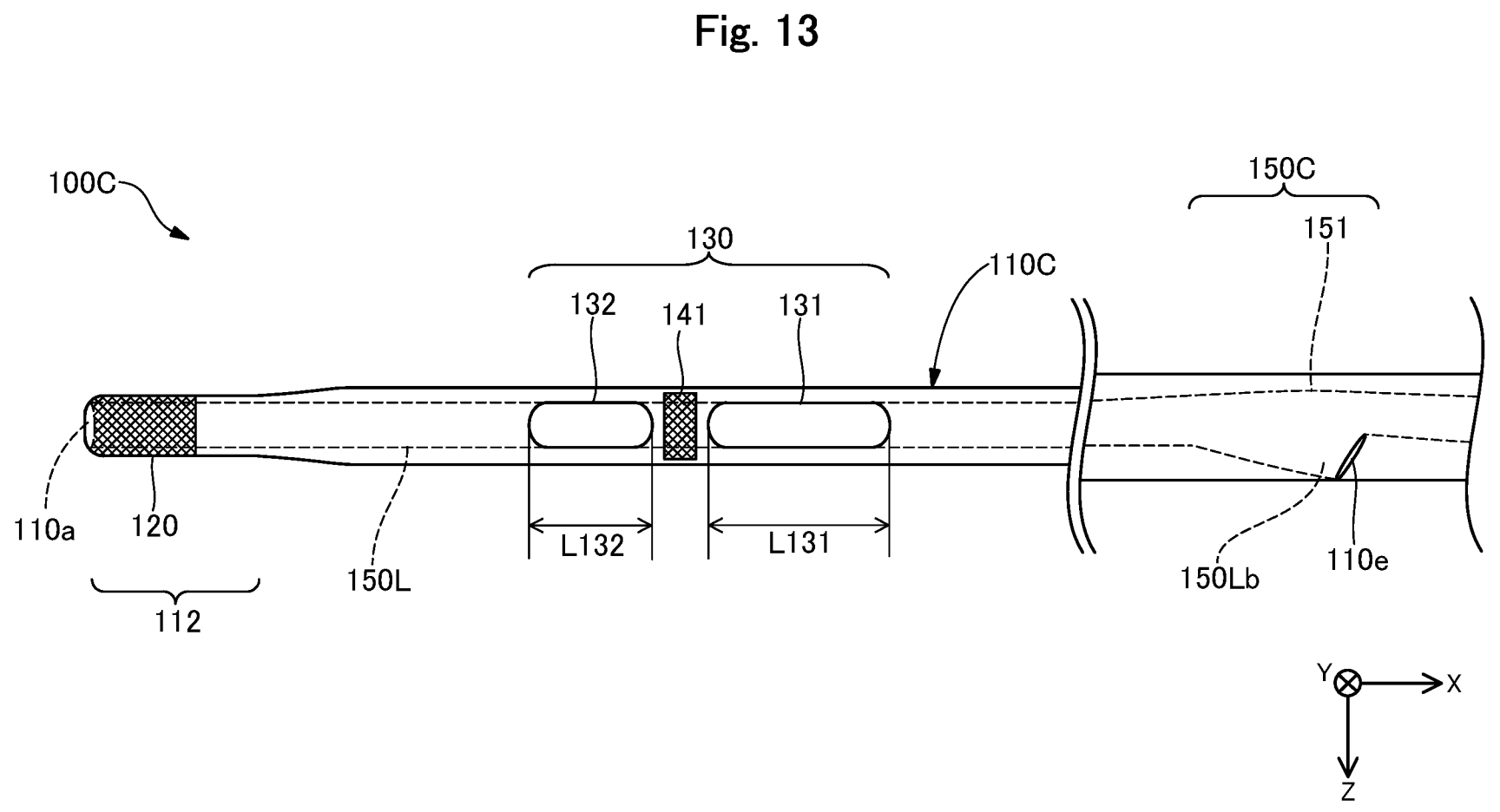

FIG. 13 is an explanatory view illustrating the configuration of a part on the distal end side of a catheter 100C according to the fourth embodiment. FIG. 13 is a bottom view of the catheter 100C viewed from the same direction as in FIG. 3. The recanalization catheter system 1 of the fourth embodiment includes the catheter 100C illustrated in FIG. 13 instead of the catheter 100 described in the first embodiment. The shaft 110C of the catheter 100C includes a branching part 150C instead of the branching part 150. The branching part 150C does not include the raised portion 152 and the boundary wall 153 that are described in the first embodiment.

In this manner, the configuration of the branching part 150C can be changed variously, and the branching part 150C may not include at least one of the raised portion 152 and the boundary wall 153, or may not include both of them. Such a catheter 100C of the fourth embodiment can also exert similar effects as in the above-described first embodiment, except the wire guiding effect in the first case and the second case.

Fifth Embodiment

Figure 14:
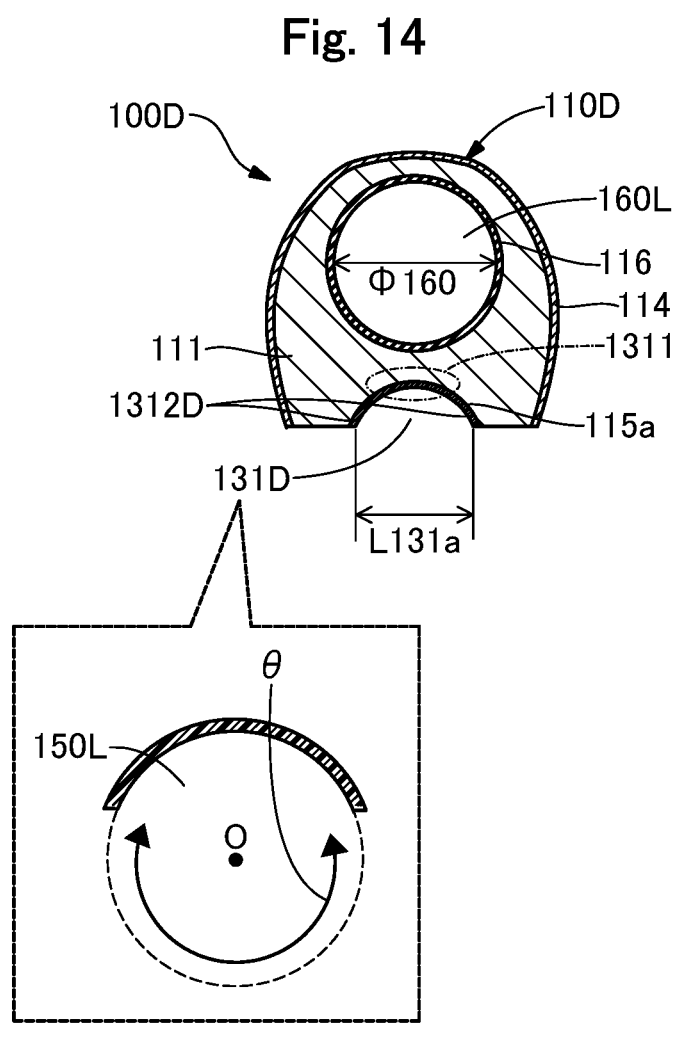

FIG. 14 is an explanatory view illustrating the configuration of a transverse section of a catheter 100D according to a fifth embodiment. FIG. 14 illustrates, in the upper stage thereof, a transverse sectional view along B2-B2 line of FIG. 2, and illustrates, in the lower stage thereof, an explanatory view of the range where a first notch 131D is provided. The recanalization catheter system 1 of the fourth embodiment includes the catheter 100D illustrated in FIG. 14 instead of the catheter 100 described in the first embodiment. A shaft 110D of the catheter 100D includes the first notch 131D instead of the first notch 131 described in the first embodiment.

The first notch 131D is formed on the same side as the first notch 131 described in the first embodiment, and is elliptical including a first short axis and a first long axis. Meanwhile, the angle of the first notch 131 in the entire circumference of the wire lumen 150L is about 180° in the first notch 131 of the first embodiment, while the angle θ of the first notch 131D in the entire circumference of the wire lumen 150L is about 240° in the first notch 131D of the fifth embodiment (lower stage in FIG. 14). Thus, a side wall 1312D of the first notch 131D is shorter than the side wall 1312 described in the first embodiment. Moreover, the length L131a of the first short axis of the first notch 131D is shorter than the inner diameter φ150 of the wire lumen 150L.

In this manner, the configuration of the first notch 131D can be changed variously, and the angle θ of the first notch 131D in the entire circumference of the wire lumen 150L can be changed arbitrarily. Similarly in the second notch 132, the angle of the second notch 132 in the entire circumference of the wire lumen 150L may be changed arbitrarily. Such a catheter 100D of the fifth embodiment can also exert similar effects as in the above-described first embodiment.

Sixth Embodiment

Figure 15:
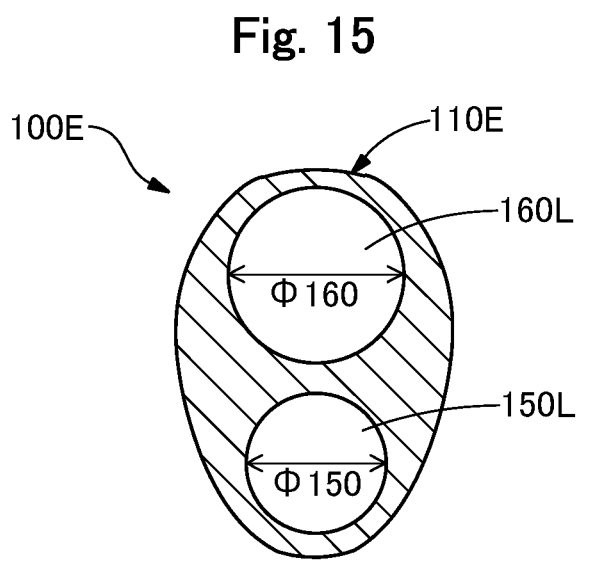

FIG. 15 is an explanatory view illustrating the configuration of a transverse section of a catheter 100E according to the sixth embodiment. FIG. 15 illustrates the configuration of the transverse section along B1-B1 line in FIG. 2. The recanalization catheter system 1 of the sixth embodiment includes the catheter 100E illustrated in FIG. 15 instead of the catheter 100 described in the first embodiment. A shaft 110E of the catheter 100E does not include the outer shaft 114, the first inner shaft 115, the second inner shaft 116, and the sealing member 111 that are described in the first embodiment, and is formed by the single shaft 110E. Except the point that the shaft 110E is formed by the single member, the shaft 110E has the same configuration as the shaft 110 described in the first embodiment. That is, the shaft 110E includes the wire lumen 150L, the sensor lumen 160L, the projection part 112, the notch part 130, and the branching part 150 that are described in the first embodiment.

In this manner, the configuration of the catheter 100E can be changed variously, and the catheter 100E may be formed only by the single shaft 110E. Moreover, the shaft 110E may not include the outer shaft 114 and the sealing member 111, and may be formed by the first inner shaft 115 and the second inner shaft 116 jointed to each other. Further, the shaft 110E may not include the sealing member 111, and may be formed by the first inner shaft 115 and the second inner shaft 116 housed in the outer shaft 114. Such a catheter 100E of the sixth embodiment can also exert similar effects as in the above-described first embodiment.

Seventh Embodiment

Figure 16:
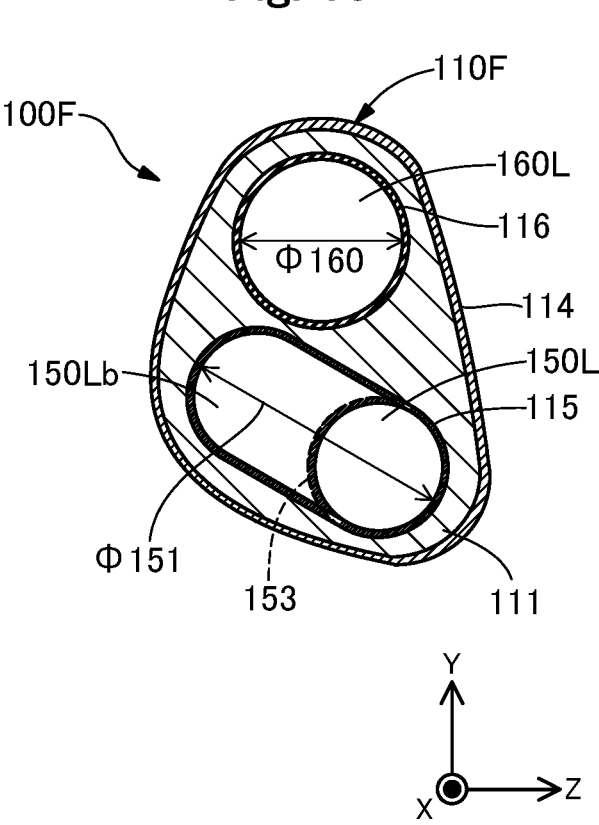
FIG. 16 is an explanatory view illustrating the configuration of a transverse section of a catheter according to a seventh embodiment.

FIG. 16 is an explanatory view illustrating the configuration of a transverse section of a catheter 100F according to the seventh embodiment. FIG. 16 illustrates the configuration of the transverse section along C-C line in FIG. 2. The recanalization catheter system 1 of the seventh embodiment includes the catheter 100F illustrated in FIG. 16 instead of the catheter 100 described in the first embodiment. In a shaft 110F of the catheter 100F, the wire lumen 150L and the branching lumen 150Lb are arranged inclined relative to the Z-axis direction.

In this manner, the configuration of the shaft 110F can be changed variously, and the arrangement of the wire lumen 150L, the branching lumen 150Lb, and the sensor lumen 160L in the shaft 110F can be changed arbitrarily. Such a catheter 100F of the seventh embodiment can also exert similar effects as in the above-described first embodiment.

Eighth Embodiment

FIGS. 17A and 17B are explanatory views illustrating the configuration of a part on the distal end side of a catheter 100G according to the eighth embodiment. FIG. 17A illustrates a side view of the catheter 100G, and FIG. 7B illustrates a bottom view of the catheter 100G. The recanalization catheter system 1 of the eighth embodiment includes the catheter 100G illustrated in FIGS. 17A and 17B instead of the catheter 100 described in the first embodiment.

A shaft 110G of the catheter 100G includes a wire lumen 150LG instead of the wire lumen 150L described in the first embodiment. The wire lumen 150LG is not branched, and extends linearly from the distal end to the proximal end of the shaft 110G. Thus, the shaft 110G does not include the branching lumen 150Lb, the port 110e, the branching part 150, the large diameter portion 151, the raised portion 152, nor the boundary wall 153 that are described in the first embodiment. In the catheter 100G of the embodiment, in the first case where the delivery guide wire 70 is inserted to the wire lumen 150LG from the distal end first opening 110a and advances in the wire lumen 150LG from the distal end side toward the proximal end side, the proximal end portion of the delivery guide wire 70 is pulled out from the proximal end first opening 110c of the shaft 110G.

In this manner, the configuration of the shaft 110G can be changed variously, and the shaft 110G may include the wire lumen 150LG that is not branched. Such a catheter 100G of the eighth embodiment can also exert similar effects as in the above-described effect example 1 of the effects described above in the first embodiment.

Ninth Embodiment

Figures 18A, 18B:
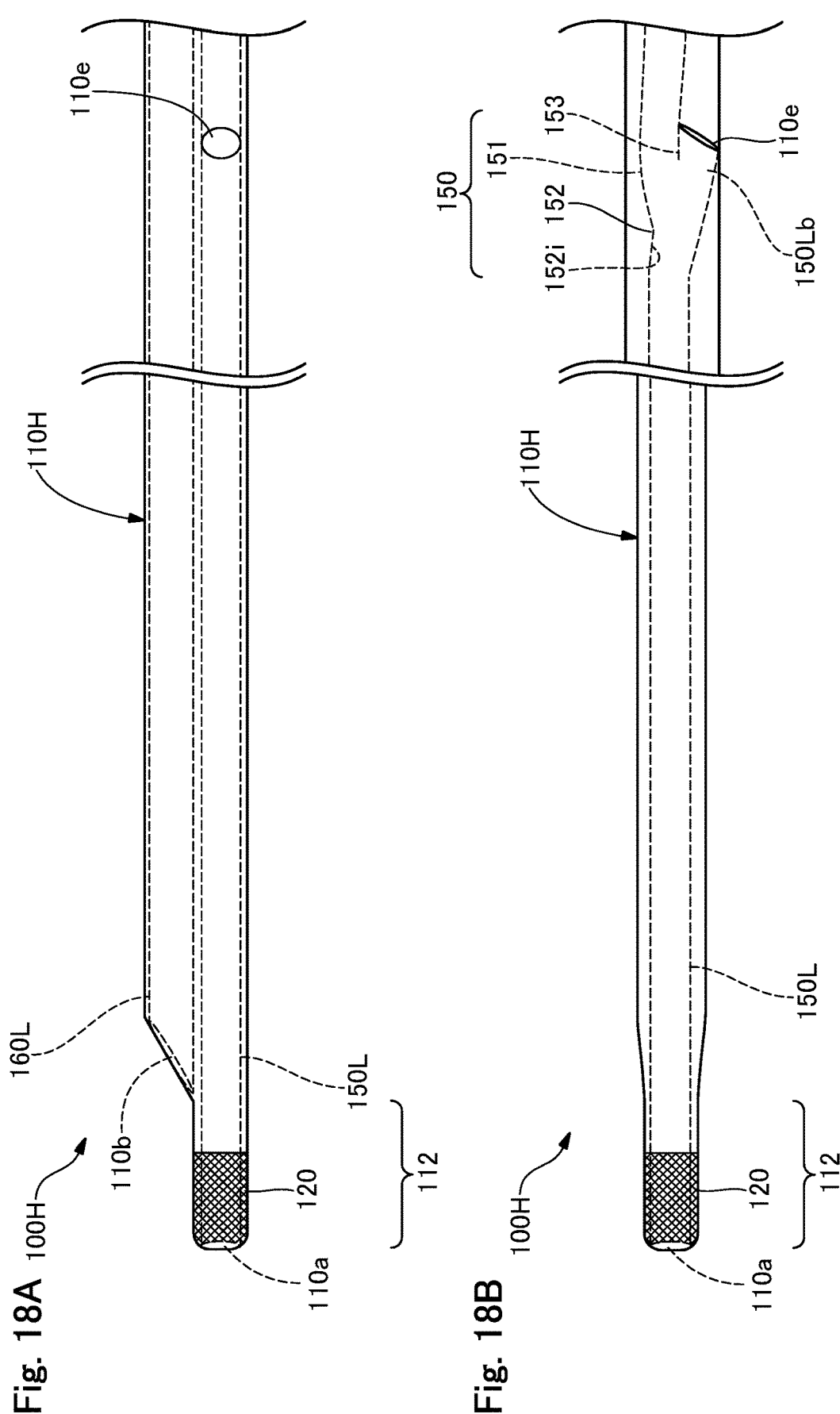
FIGS. 18A and 18B are explanatory views illustrating the configuration of a part on the distal end side of a catheter according to a ninth embodiment.

FIGS. 18A and 18B are explanatory views illustrating the configuration of a part on the distal end side of a catheter 100H according to the ninth embodiment. FIG. 18A illustrates a side view of the catheter 100H, and FIG. 18B illustrates a bottom view of the catheter 100H. The recanalization catheter system 1 of the ninth embodiment includes the catheter 100H illustrated in FIGS. 18A and 18B instead of the catheter 100 described in the first embodiment.

A shaft 110H of the catheter 100H does not include the notch part 130 (first notch 131, second notch 132) described in the first embodiment. In the catheter 100H of the embodiment, in the second case where the penetration guide wire 400 is inserted to the wire lumen 150L from the proximal end first opening 110c and advances in the wire lumen 150L from the proximal end side toward the distal end side, the distal end portion of the penetration guide wire 400 projects from the distal end first opening 110a of the shaft 110H.

In this manner, the configuration of the shaft 110H can be changed variously, and the shaft 110H may not include the notch part 130. Such a catheter 100H of the ninth embodiment can also exert similar effects as in the above-described effect example 2 of the effects described above in the first embodiment.

MODIFICATION EXAMPLES OF THE EMBODIMENTS

The embodiments are not limited to those disclosed above, and can be implemented in various aspects without departing from the gist thereof. For example, the following modification examples are also possible.

Modification Example 1

The above first to ninth embodiments show examples of the configurations of the recanalization catheter system 1. However, the configurations of the recanalization catheter system 1 can be variously changed. For example, as the imaging sensor 200, there may be used a sensor that acquires images of living tissues by a method other than transmission and reception of ultrasonic waves. Moreover, an optical coherence tomography (OCT) or a camera, instead of the imaging sensor 200, may be inserted to acquire images of living tissues in blood vessels.

For example, the recanalization catheter system 1 may be formed as a system for CTO recanalization using a plasma guide wire for ablation of living tissues utilizing plasma, instead of using the penetration guide wire 400. In this case, in the catheters 100, 100A to 100H, an electrode is preferably provided at the distal end portion of the shaft 110. In this manner, with high-frequency power output between an electrode provided at the distal end portion of the shaft 110 and a distal end electrode of a plasma guide wire, ablation of living tissues is possible using energy emitted by discharge between the both electrodes. Note that the electrode at the distal end portion of the shaft 110 is preferably arranged on the more proximal end side than the distal tip 120 and the more distal end side than the notch part 130.

For example, the recanalization catheter system 1 may be used in a method other than the above-described methods. For example, the recanalization catheter system may be used in a blood vessel other than the coronary artery (for example, a cerebral blood vessel or the like), and may be used in a living body lumen other than blood vessels. For example, the recanalization catheter system 1 may be used in therapeutics other than the recanalization catheter system, or in examinations.

Modification Example 2

The above first to ninth embodiments show examples of the configurations of the catheters 100, 100A to 100H. However, the configurations of the catheters 100, 100A to

100H can be various changed. For example, the wire lumen 150L and the sensor lumen 160L of the catheter 100 may have a substantially same diameter, or the wire lumen 150L may be configured to have a smaller diameter than the sensor lumen 160L. For example, the catheter 100 may further include, in addition to the wire lumen 150L and the sensor lumen 160L, a lumen for another medical device or for the delivery guide wire 70 and the penetration guide wire 400 to be inserted at the same time.

For example, the distal end P1 (lower stage of FIG. 3) of the boundary wall 153 may be positioned on the more proximal end side than the distal end P2 of the port 110e. For example, the length L153 (lower stage of FIG. 3) in the longitudinal direction of the shaft 110 of the boundary wall 153 may be smaller than the length L110 in the longitudinal direction of the shaft 110 of the port 110e. For example, at least any of the outer surfaces of the shaft 110, 110A to 110H, the outer surface or the inner surface of the first inner shaft 115, the outer surface or the inner surface of the second inner shaft 116, and the outer surface or the inner surface of the outer shaft 114 may be coated with an arbitrary resin layer (for example, a hydrophilic resin layer, a hydrophobic resin layer, an underlayer for improving joinability of a hydrophilic resin layer and a hydrophobic resin layer, or the like), or a chemical agent may be applied on the surface.

Modification Example 3

The configurations of the catheters 100, 100A to 100H of the first to ninth embodiments, and the configurations of the catheters 100, 100A to 100H of the above-described modification examples 1, 2 may be combined appropriately. For example, the catheter 100G described in the eighth embodiment may have the configuration described in the second, third, fourth, or seventh embodiment. For example, the catheter 100H described in the ninth embodiment may have the configuration described in the fourth embodiment. For example, the catheters 100A, B described in the second or third embodiment may have the configuration described in the fifth or seventh embodiment. For example, the catheters 100A to D, F to H described in the second to fifth and the seventh to ninth embodiments may have the configuration described in the sixth embodiment.

In the above, the present aspects are described on the basis of the embodiments and the modification examples. However, the embodiments of the aforementioned aspects are provided to facilitate understanding of the present aspects, and do not limit the present aspects. The present aspects may be altered or improved without departing from the spirit thereof and claims, and the present aspects include their equivalents. Further, the technical features thereof, if not indicated as essential in the present specification, may be appropriately deleted.

What is claimed is:

1. A catheter having a shaft, the shaft comprising:
   a wire lumen that extends in a longitudinal direction of the shaft;
   a sensor lumen that is arranged side by side with the wire lumen;
   a projection part that includes the wire lumen, projects to a more distal side than a distal end of the sensor lumen, and has a distal end opening in communication with the wire lumen at a distal end of the projection part;
   a first notch that is a notch formed on a more proximal end side than the projection part, and is in communication with the wire lumen, wherein the first notch is formed on a side surface of the shaft, the side surface being positioned on an opposite side of the sensor lumen relative to a center axis of the wire lumen, and the shaft includes, in a section including the first notch, a bottom portion facing the first notch and a pair of side walls extending from the bottom portion to the opposite side of the sensor lumen;

a branching lumen between a distal end and a proximal end of the shaft the branching lumen extending from the wire lumen; and a branching part that is formed at a connection portion between the wire lumen and the branching lumen, wherein:

a distal end side of the branching lumen is connected to the wire lumen, a proximal end side of the branching lumen is positioned on a more proximal end side of the shaft than a distal end side, the proximal end side of the branching lumen is in communication with an outside through a port formed on a side surface of the shaft, and the branching part includes:

a large diameter portion with an inner diameter larger than an inner diameter of the wire lumen, a boundary wall separating the wire lumen and the branching lumen from each other on a more proximal end side than the large diameter portion, and a raised portion that is raised toward a side of the extending branching lumen, in an area on a more distal end side than the large diameter portion and on an opposite side of the extending branching lumen, in an inner peripheral surface defining the wire lumen.

2. The catheter according to claim 1, wherein the first notch has an elliptical shape including a first long axis extending along the center axis of the wire lumen and a first short axis extending vertically to the center axis in side view of the wire lumen, and a length of the first short axis is equal to an inner diameter of the wire lumen.

3. The catheter according to claim 1, wherein the shaft further comprises a second notch that is a notch formed on a more distal end side or the more proximal end side than the first notch, and is in communication with the wire lumen, the second notch is formed on the side surface of the shaft, the side surface being on a same side as the first notch, and the shaft includes, in a section with the second notch, a bottom portion facing the second notch and a pair of side walls extending from the bottom portion to the opposite side of the sensor lumen.

4. The catheter according to claim 3, wherein the second notch has an elliptical shape including a second long axis extending along the center axis of the wire lumen and a second short axis extending vertically to the center axis in side view of the wire lumen, and a length of the second short axis is equal to the inner diameter of the wire lumen and a length of the second long axis is shorter than a length of the first long axis of the first notch.

5. The catheter according to claim 1, wherein the port is inclined relative to the center axis of the shaft, and a distal end of the boundary wall is positioned at the same position as a distal end of the port or on the more distal end side than the distal end of the port in the longitudinal direction of the shaft.

6. The catheter according to claim 1, wherein a length in the longitudinal direction of the shaft of the boundary wall is equal to or longer than a length in the longitudinal direction of the shaft of the port.

7. The catheter according to claim 1, wherein, in a first case that a wire is inserted to the wire lumen from the distal end opening, a proximal end portion of the wire is brought into contact with the raised portion and guided toward the branching lumen, and in a second case that a wire is inserted to the wire lumen from the proximal end side of the shaft, the distal end portion of the wire is brought into contact with the boundary wall to suppress advancement of the distal end portion of the wire toward the branching lumen.

8. The catheter according to claim 2, wherein the shaft further comprises a second notch that is a notch formed on a more distal end side or the more proximal end side than the first notch, and is in communication with the wire lumen, the second notch is formed on the side surface of the shaft, the side surface being on a same side as the first notch, and the shaft includes, in a section with the second notch, a bottom portion facing the second notch and a pair of side walls extending from the bottom portion to the opposite side of the sensor lumen.

9. The catheter according to claim 8, wherein the second notch has an elliptical shape including a second long axis extending along the center axis of the wire lumen and a second short axis extending vertically to the center axis in side view of the wire lumen, and a length of the second short axis is equal to the inner diameter of the wire lumen and a length of the second long axis is shorter than a length of the first long axis of the first notch.

* * * * *